US00RE44835E

(19) United States
(12) Reissued Patent
Fraser et al.

(10) Patent Number: US RE44,835 E
(45) Date of Reissued Patent: *Apr. 8, 2014

(54) MEDICAL INSTALLATION TOOL

(75) Inventors: Robert D. Fraser, Adelaide (AU); Alexander Grinberg, Newton, MA (US); John D. Malone, Franklin, MA (US); Bradley Moore, West Vancouver (CA); Michael J. O'Neil, West Barnstable, MA (US); Mark C. Boomer, Phoenix, AZ (US)

(73) Assignee: DePuy Synthes Products LLC, Raynham, MA (US)

( * ) Notice: This patent is subject to a terminal disclaimer.

(21) Appl. No.: 13/331,675

(22) Filed: Dec. 20, 2011

Related U.S. Patent Documents

Reissue of:
(64) Patent No.: 6,755,841
Issued: Jun. 29, 2004
Appl. No.: 10/011,264
Filed: Dec. 7, 2001

U.S. Applications:
(63) Continuation of application No. 11/397,887, filed on Mar. 29, 2006, now Pat. No. Re. 43,317, which is a continuation-in-part of application No. 09/566,514, filed on May 8, 2000, now Pat. No. 6,478,800.

(51) Int. Cl.
*A61B 17/58* (2006.01)

(52) U.S. Cl.
USPC ..... 606/99

(58) Field of Classification Search
USPC ..... 606/53, 86, 86 A, 86 B, 99, 100, 606/106–108, 119, 123–124, 205–206, 606/210–211; 600/237–244
See application file for complete search history.

(56) References Cited

U.S. PATENT DOCUMENTS 3,409,013 A * 11/1968 Berry ..... 606/1
3,486,505 A 12/1969 Morrison (Continued)

FOREIGN PATENT DOCUMENTS

DE 29901611 4/1999
DE 29901611 U 4/1999

(Continued)

OTHER PUBLICATIONS

[No Author Listed] Metronic, "Parallel Tissue Offerings," (2004).

(Continued)

*Primary Examiner* — Nicholas Woodall
(74) *Attorney, Agent, or Firm* — Nutter McClennen & Fish LLP

(57) ABSTRACT

An installation tool that is useful for the efficient and effective placement of an article, such as an artificial disc, between adjacent vertebral bodies is provided. The installation tool can be provided as a kit having modular components which allow the surgeon to select from among a variety of components to assemble an installation tool that is optimized for its intended use. The installation tool of the invention generally includes a pair of opposed levers, each of which has a proximal handle portion and a distal portion. A fulcrum is disposed between the two levers to enable proper operation of the tool. The tool further includes a pusher block that is positioned between the two levers and is selectively movable between an initial location distal of the fulcrum and a final location adjacent the distal end of the levers. The pusher block includes a proximal end, a distal end, and a bore extending at least partially therethrough. A pusher rod, which facilitates movement of a pusher block, has a distal end extending into the bore in the pusher block and a proximal, handle end.

16 Claims, 19 Drawing Sheets

(56) References Cited

U.S. PATENT DOCUMENTS

| | | | |
|---|---|---|---|
| 4,034,746 | A | 7/1977 | Williams |
| 4,337,576 | A | 7/1982 | Drost et al. |
| 4,369,788 | A | 1/1983 | Goald |
| 4,444,184 | A | 4/1984 | Oretorp |
| 4,545,374 | A | 10/1985 | Jacobson |
| 4,660,287 | A | 4/1987 | Decker |
| 4,730,613 | A | 3/1988 | Gordy |
| 4,735,202 | A | 4/1988 | Williams |
| 4,772,287 | A | 9/1988 | Ray et al. |
| 4,877,020 | A | 10/1989 | Vich et al. |
| 4,898,161 | A | 2/1990 | Grundei |
| 4,997,432 | A | 3/1991 | Keller |
| 5,015,247 | A | 5/1991 | Michelson |
| 5,019,081 | A | 5/1991 | Watanabe |
| 5,020,519 | A | 6/1991 | Hayes et al. |
| 5,052,373 | A | 10/1991 | Michelson |
| 5,055,104 | A | 10/1991 | Ray |
| 5,059,194 | A | 10/1991 | Michelson |
| 5,122,130 | A | 6/1992 | Keller |
| 5,139,507 | A | 8/1992 | Dolgin et al. |
| 5,213,112 | A | 5/1993 | Niwa et al. |
| 5,254,128 | A | 10/1993 | Mesa |
| 5,292,329 | A | 3/1994 | Werner |
| 5,304,119 | A | 4/1994 | Balaban et al. |
| 5,306,309 | A | 4/1994 | Wagner et al. |
| 5,314,477 | A | 5/1994 | Marnay |
| 5,403,337 | A | 4/1995 | Platts |
| 5,423,843 | A | 6/1995 | Werner |
| 5,431,658 | A | 7/1995 | Moskovich |
| 5,431,672 | A | 7/1995 | Cote et al. |
| 5,443,514 | A | 8/1995 | Steffee |
| 5,481,804 | A | 1/1996 | Platts |
| 5,484,437 | A | 1/1996 | Michelson |
| 5,496,340 | A | 3/1996 | Abidin et al. |
| 5,505,732 | A | 4/1996 | Michelson |
| 5,531,754 | A | 7/1996 | Shackelford, Sr. et al. |
| 5,562,736 | A | 10/1996 | Ray et al. |
| 5,569,281 | A | 10/1996 | Abidin et al. |
| 5,569,282 | A | 10/1996 | Werner |
| 5,571,109 | A | 11/1996 | Bertagnoli |
| 5,599,351 | A | 2/1997 | Haber et al. |
| 5,620,454 | A | 4/1997 | Pierce et al. |
| 5,645,597 | A | 7/1997 | Krapiva |
| 5,665,099 | A | 9/1997 | Pilo et al. |
| 5,683,407 | A | 11/1997 | Jolly et al. |
| 5,683,464 | A | 11/1997 | Wagner et al. |
| 5,720,751 | A | 2/1998 | Jackson |
| 5,722,977 | A | 3/1998 | Wilhelmy |
| 5,730,751 | A | 3/1998 | Dillon et al. |
| 5,741,253 | A | 4/1998 | Michelson |
| 5,752,968 | A | 5/1998 | Jolly et al. |
| 5,766,252 | A | 6/1998 | Henry et al. |
| 5,779,724 | A | 7/1998 | Werner |
| 5,782,830 | A | 7/1998 | Farris |
| 5,792,162 | A | 8/1998 | Jolly et al. |
| 5,797,909 | A | 8/1998 | Michelson |
| 5,800,438 | A | 9/1998 | Tuke et al. |
| 5,827,309 | A | 10/1998 | Jolly et al. |
| 5,868,771 | A | 2/1999 | Herbert et al. |
| 5,885,299 | A | 3/1999 | Winslow et al. |
| 5,885,300 | A | 3/1999 | Tokuhashi et al. |
| 5,888,224 | A | 3/1999 | Beckers et al. |
| 5,899,901 | A | 5/1999 | Middleton |
| 5,908,432 | A | 6/1999 | Pan |
| 5,935,151 | A | 8/1999 | Broughton et al. |
| 5,944,658 | A | 8/1999 | Koros et al. |
| 5,951,564 | A | 9/1999 | Schroder et al. |
| 5,957,927 | A | 9/1999 | Magee et al. |
| 6,004,326 | A | 12/1999 | Castro et al. |
| 6,015,419 | A | 1/2000 | Strome et al. |
| 6,022,364 | A | 2/2000 | Flumene et al. |
| 6,042,582 | A | 3/2000 | Ray |
| 6,063,088 | A | 5/2000 | Winslow |
| 6,066,174 | A | 5/2000 | Farris |
| 6,080,155 | A | 6/2000 | Michelson |
| 6,083,225 | A | 7/2000 | Winslow et al. |
| 6,083,228 | A | 7/2000 | Michelson |
| 6,096,038 | A | 8/2000 | Michelson |
| 6,113,602 | A | 9/2000 | Sand |
| 6,117,174 | A | 9/2000 | Nolan |
| 6,133,602 | A | 10/2000 | Shrivastava et al. |
| RE37,005 | E | 12/2000 | Michelson et al. |
| 6,156,040 | A | 12/2000 | Yonemura et al. |
| 6,159,212 | A | 12/2000 | Schoedinger, III et al. |
| 6,159,215 | A | 12/2000 | Urbahns et al. |
| 6,159,244 | A | 12/2000 | Suddaby |
| 6,168,601 | B1 | 1/2001 | Martini |
| 6,197,033 | B1 | 3/2001 | Haid, Jr. et al. |
| 6,200,322 | B1 | 3/2001 | Branch et al. |
| 6,261,296 | B1 | 7/2001 | Aebi et al. |
| 6,267,763 | B1 | 7/2001 | Castro |
| 6,277,122 | B1 | 8/2001 | McGahan |
| 6,319,257 | B1 | 11/2001 | Carignan et al. |
| 6,436,119 | B1 | 8/2002 | Erb et al. |
| 6,440,142 | B1 | 8/2002 | Ralph et al. |
| 6,478,800 | B1 | 11/2002 | Fraser et al. |
| 6,520,967 | B1 | 2/2003 | Cauthen |
| 6,551,316 | B1 | 4/2003 | Rinner et al. |
| 6,575,981 | B1 | 6/2003 | Boyd et al. |
| 6,582,437 | B2 | 6/2003 | Dorchak et al. |
| 6,589,247 | B2 | 7/2003 | McGahan et al. |
| 6,599,291 | B1 | 7/2003 | Foley et al. |
| 6,599,294 | B2 | 7/2003 | Fuss et al. |
| 6,648,888 | B1 | 11/2003 | Shluzas |
| 6,648,895 | B2 | 11/2003 | Burkus et al. |
| 6,663,638 | B2 | 12/2003 | Ralph |
| 6,712,825 | B2 | 3/2004 | Aebi et al. |
| 6,719,760 | B2 | 4/2004 | Dorchak et al. |
| 6,743,234 | B2 | 6/2004 | Burkus et al. |
| 6,755,841 | B2 | 6/2004 | Fraser et al. |
| 6,814,737 | B2 | 11/2004 | Cauthen |
| 7,118,580 | B1 | 10/2006 | Beyersdorff et al. |
| RE43,317 | E | 4/2012 | Fraser et al. |
| 2001/0029377 | A1 | 10/2001 | Aebi et al. |
| 2001/0031968 | A1 | 10/2001 | Dorchak et al. |
| 2001/0031969 | A1 | 10/2001 | Aebi et al. |
| 2002/0116009 | A1 | 8/2002 | Fraser et al. |
| 2002/0123754 | A1 | 9/2002 | Holmes et al. |
| 2002/0143343 | A1 | 10/2002 | Castro |
| 2002/0198532 | A1 | 12/2002 | Michelson |
| 2003/0069586 | A1 | 4/2003 | Errico et al. |
| 2003/0078590 | A1 | 4/2003 | Errico et al. |
| 2003/0149438 | A1 | 8/2003 | Nichols et al. |
| 2003/0212404 | A1 | 11/2003 | Dorchak et al. |
| 2003/0225416 | A1 | 12/2003 | Bonvallet et al. |
| 2004/0039397 | A1 | 2/2004 | Weber et al. |
| 2004/0078079 | A1 | 4/2004 | Foley |
| 2004/0102790 | A1 | 5/2004 | Ralph et al. |
| 2004/0106927 | A1 | 6/2004 | Ruffner et al. |
| 2004/0117019 | A1 | 6/2004 | Trieu et al. |
| 2004/0167535 | A1 | 8/2004 | Errico et al. |
| 2004/0167536 | A1 | 8/2004 | Errico et al. |
| 2004/0172037 | A1 | 9/2004 | Dorchak |
| 2004/0225295 | A1 | 11/2004 | Zubok et al. |
| 2005/0010213 | A1 | 1/2005 | Stad et al. |
| 2005/0027300 | A1 | 2/2005 | Hawkins et al. |
| 2005/0043741 | A1 | 2/2005 | Michelson |
| 2005/0075644 | A1 | 4/2005 | DiPoto et al. |
| 2005/0119665 | A1 | 6/2005 | Keller |
| 2005/0143747 | A1 | 6/2005 | Zubok et al. |
| 2005/0159756 | A1 | 7/2005 | Ray |
| 2005/0165408 | A1 | 7/2005 | Puno et al. |

FOREIGN PATENT DOCUMENTS

| | | |
|---|---|---|
| DE | 29916078 | 11/1999 |
| DE | 29916078 U | 11/1999 |
| DE | 20012549 | 10/2000 |
| DE | 20012549 U | 10/2000 |
| EP | 0880938 | 12/1998 |

(56) References Cited

FOREIGN PATENT DOCUMENTS

| | | | |
|---|---|---|---|
| EP | 1 153 582 | A2 | 11/2001 |
| WO | 0074605 | A1 | 12/2000 |
| WO | WO 00/74605 | | 12/2000 |

OTHER PUBLICATIONS

[No Author Listed] Metronic Sofamor Danek, "Catalyst Anterior Instrument Set," pp. 1-10 (2004).

Capasso, G. Velotti A. and Auzino, G., "Mechanical Behavior of Two Types of Vertebral Distractors Submitted to Compression-Flexion Tests," Ital J. Orthop Traumatol. 13(1):121-6 (1987).

Demetropoulas, C.K., Truumees, E., Herkowitz, H.N. and Yang, K.H., "Development and calivration of a load sensing cervical distractor capable of withstanding autoclave sterilization," Med Eng Phys. 27(4):343-6 (2005).

Rutsky, V.V. and Valkav, A.N., "Designing a dynamic spinal distractor," Med Tekh. 4:29-32 (1995).

Technical Manual "Keystone Graft Instruments Anterior Cervical Surgical Technique", Depuy Motech.

* cited by examiner

FIG. 11
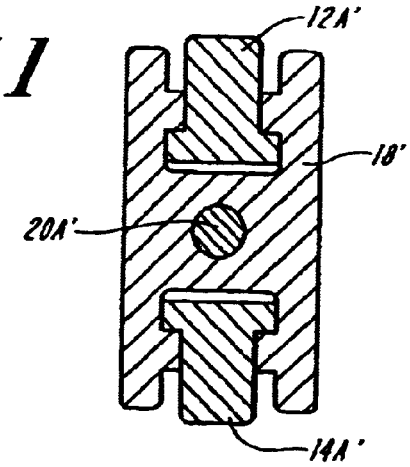
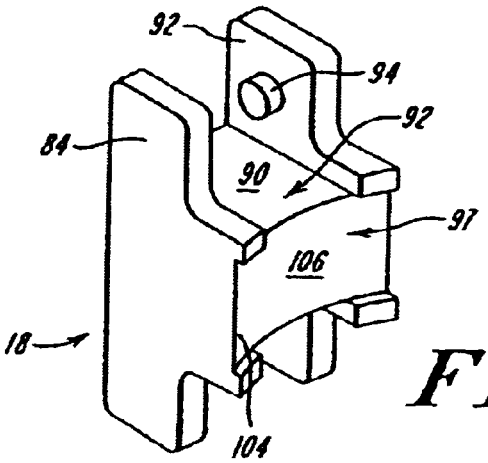
FIG. 12
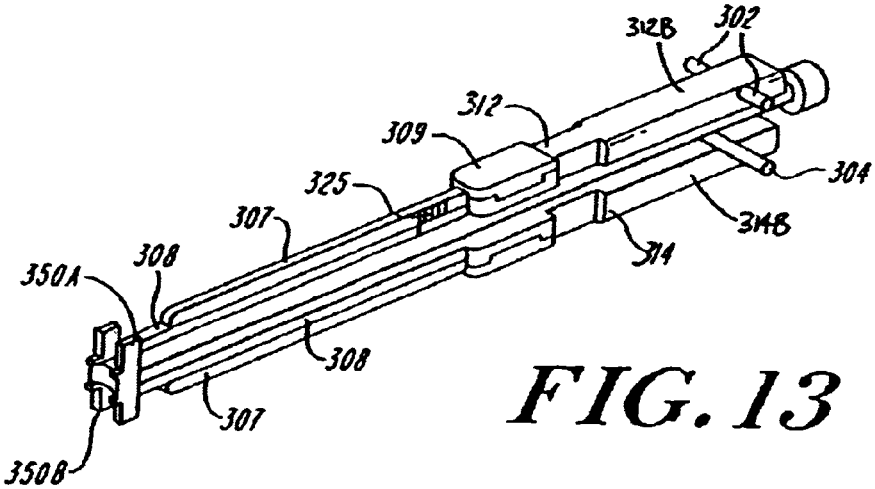
FIG. 13

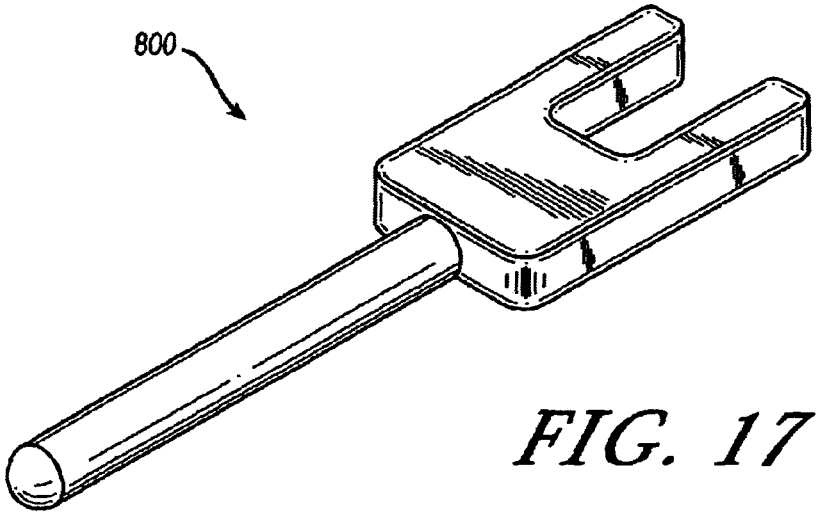
FIG. 17
FIG. 18
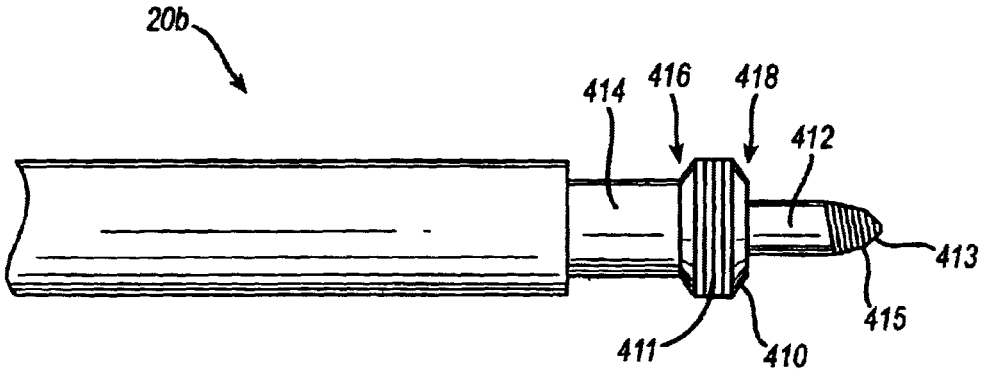

MEDICAL INSTALLATION TOOL

Matter enclosed in heavy brackets [ ] appears in the original patent but forms no part of this reissue specification; matter printed in italics indicates the additions made by reissue.

CROSS-REFERENCE TO RELATED APPLICATIONS

[This application] *More than one reissue application has been filed for the reissue of U.S. Pat. No. 6,755,841. This application is a continuation reissue of U.S. patent application Ser. No. 11/397,887, filed on Mar. 29, 2006, now U.S. Pat. No. Re. 43,317, which is a reissue of U.S. patent application Ser. No. 10/011,264, filed on Dec. 7, 2001, now U.S. Pat. No. 6,755,841, which* is a continuation-in-part of U.S. patent application Ser. No. 09/566,514, filed on May 8, 2000, now U.S. Pat. No. 6,478,800 entitled "Medical Installation Tool," *the entire contents of each of* which is *hereby* expressly incorporated herein by reference.

BACKGROUND OF THE INVENTION

The invention relates to a tool for inserting prostheses within the body, and more particularly to tools for inserting prostheses, such as artificial discs and cages, within an intervertebral space.

Spinal surgery involves many challenges as the long-term health and mobility of the patient often depends on the surgeon's technique and precision. One type of spinal surgery involves the removal of the natural disc tissue that is located between adjacent vertebral bodies. Procedures are known in which the natural, damaged disc tissue is replaced with an interbody cage or fusion device, or with a disc prosthesis.

The insertion of an article, such as an artificial disc prosthesis, presents the surgeon with several challenges. The adjacent vertebral bodies collapse upon each other once the natural disc tissue is removed. These bodies must be separated to an extent sufficient to enable the placement of the prosthesis. However, if the vertebral bodies are separated, or distracted, to beyond a certain degree, further injury can occur. The disc prosthesis must also be properly positioned between the adjacent vertebral bodies. Over-insertion, or under-insertion of the prosthesis can lead to pain, postural problems and/or limited mobility or freedom of movement.

Specialized tools have been developed to facilitate the placement of devices, such as disc prosthesis, between adjacent vertebral bodies of a patient's spine. Among the known tools for performing such procedures are separate spinal distractors and insertion devices. The use of separate tools to distract the vertebral bodies and insert a disc prosthesis or graft can prove cumbersome. Further, the use of some distractors can cause over-distraction of the vertebral bodies.

Exemplary devices for installing prosthesis and/or grafts between vertebral bodies are disclosed in U.S. Pat. Nos. 5,431,658 and 5,505,732. U.S. Pat. No. 5,431,658 discloses a facilitator device for the insertion of bone grafts between two adjacent vertebrae. The disclosed tool has two flat, tong-like guides that distract the vertebrae as a screw-type inserter forces the graft between the distracted vertebrae. U.S. Pat. No. 5,505,732 discloses an apparatus and a method of inserting spinal implants. The intervertebral space is first distracted and a hollow sleeve having teeth at one end is then driven into the vertebrae that are adjacent the disc space. A drill is then passed through the hollow sleeve, removing the disc and the bone in preparation for receiving the spinal implant, which is then inserted through the sleeve.

Despite existing tools and technologies, there remains a need to provide a device to facilitate the proper and convenient insertion of an object, such as a disc prosthesis, between adjacent vertebral bodies while minimizing the risk of further injury to the patient.

SUMMARY OF THE INVENTION

The present invention provides a device useful for implanting prostheses, such as artificial spinal discs and cages, within a patient in a safe and efficient manner. The installation tool of the invention generally includes a pair of opposed levers, each of which has a proximal handle portion and a distal portion. A fulcrum is disposed between the two levers to enable proper operation of the tool. The tool further includes a pusher block that is positioned between the two levers and is selectively movable between an initial location distal of the fulcrum and a final location adjacent the distal end of the levers. The pusher block includes a proximal end, a distal end, and a bore extending at least partially therethrough. A pusher rod, which facilitates movement of a pusher block, has a distal end extending into the bore in the pusher block and a proximal, handle end.

The pusher rod and/or pusher block can be adapted to mate to a variety of prosthesis devices. In one embodiment, the pusher block can include a blind bore and a distal end of the pusher rod can mate with the blind bore in the pusher block. The pusher block can thus include a distally facing surface having surface features adapted to conform to or mate with complementary surface features on a prosthesis. In another embodiment, the bore can extend entirely through the pusher block to allow a distal end of the pusher rod to extend through the bore in the pusher block. The pusher rod can thus include a distal tip that is effective to mate to a prosthesis.

In yet another embodiment, the rod can include a first externally threaded distal portion and a second externally threaded distal portion. The second distal portion is positioned proximal to the first distal portion, and has a diameter greater than a diameter of the first distal portion. The bore of the pusher block can include a threaded proximal opening, a distal opening, and a chamber formed therebetween. The proximal opening is threadingly matable with the second distal portion of the rod to allow the second distal portion of the rod to be threadingly inserted through the proximal opening and positioned within the chamber. The diameter of the distal opening of the pusher block should be less than the diameter of the proximal opening of the pusher block to prevent the second threaded portion of the rod from extending through the distal opening in the pusher block. The threaded second distal portion is preferably freely rotatable within the chamber of the pusher block. The threaded first distal portion of the rod extends through the distal opening in the pusher block and includes a distal tip which is adapted to mate to a prosthesis.

In other aspects of the invention the bore extends entirely through the pusher block and a distal tip of the pusher rod is adapted to extend through the bore in the pusher block. The distal tip of the pusher rod is further adapted to mate to a grasping element effective to releasably engage a prosthesis. The grasping element can include an elongate proximal portion with a bore formed therein and a distal portion that is effective to releasably engage a prosthesis. The proximal portion has an outer diameter that is adapted to fit within the bore of the distal end of the pusher block. The distal portion of the grasping can include opposed first and second components that are movable between a first, open position, and a second, closed position that is effective to engage a prosthesis. In use, the distal end of the rod threadingly engages the bore of the grasping element. Rotation of the rod in a first direction is effective to cause the elongate proximal portion of the grasping element to move proximally within the bore of the pusher block, thereby moving the first and second components to the second, closed position. Rotation of the rod in a second, opposed direction is effective to cause the elongate proximal portion of the grasping element to move distally out of the bore of the pusher block and move the first and second components to the first, open position. The first and second components can optionally include at least one surface feature effective to engage a prosthesis.

In yet another embodiment, a medical device installation kit can be provided having a pair of opposed levers, a fulcrum disposed between the levers for allowing pivotal movement of the levers with respect to each other, and a plurality of prosthesis installation assemblies. Each assembly is adapted to be slidably disposed between the levers and movable between a first, proximal position and a second, distal portion. A handle portion can be provided on each assembly for moving the prosthesis installation assembly between the first and second positions. Each assembly further includes a distal prosthesis effecting element adapted to place a prosthesis between adjacent bone structures.

In one embodiment, one of the prosthesis installation assemblies includes a pusher block having a proximal end, a distal end, and a bore extending therethrough, a pusher rod slidably disposed between the levers and extending through the bore in the pusher block, and a grasping element effective to releasably engage a prosthesis. In another embodiment, one of the prosthesis installation assemblies includes a pusher rod having a proximal handle portion and a distal portion having a distal tip adapted to positively engage a prosthesis. A pusher block can be provided having a bore extending therethrough and adapted to receive a distal portion of the pusher rod. In yet another embodiment, one of the prosthesis installation assemblies can include a pusher rod having an externally threaded first distal portion and an externally threaded second distal portion. The second distal portion has a diameter greater than the first distal portion, and is positioned proximal to the first distal portion. The assembly further includes a pusher block having a bore extending entirely therethrough having a threaded proximal opening that is threadingly matable with the second distal portion of the rod, and a distal opening having a diameter less than the diameter of the second distal portion of the rod. A chamber having a diameter greater than the diameter of the second distal portion of the pusher rod is disposed between the first and second openings of the pusher block. In other aspects, one of the prosthesis installation assemblies can include a pusher block having a bore extending therethrough, a pusher rod extending through the bore in the pusher block, and a plurality of connector elements having a proximal portion adapted to mate to a distal tip of the pusher rod, and a distal portion adapted to mate to a prosthesis.

The installation tool of the invention can be used in the following manner. Once the natural, damaged disc tissue is removed from a patient and the area is prepared to receive an artificial prosthesis, such as an artificial disc, the artificial disc is loaded between the levers of the installation tool so that a posterior side of the disc abuts a distal end of the pusher block. The distal tip of the levers is then positioned between the vertebral bodies such that the outwardly facing surfaces of each lever contacts opposed vertebral bodies. Once this position is achieved, the pusher rod is advanced distally, causing the pusher block and the artificial disc to likewise move distally along the inner surfaces of the levers. As the artificial disc and the pusher rod move distally, or forward, the levers separate and also cause vertical separation of the adjacent vertebral bodies. To achieve the proper position of the artificial disc, the distal facing surfaces of the pusher block should contact the vertebral bodies. Once such contact is achieved between the distal facing surfaces of the pusher block and the vertebral bodies, the artificial disc is properly positioned. This tool thus enables the proper positioning of the artificial disc between the vertebral bodies, without over-insertion or under-insertion of the artificial disc, while minimizing the degree of distraction of the vertebrae. To remove the tool, a slaphammer or similar device can be used to apply a proximally directed force to the tool to extract the blade tips without removing the implant.

BRIEF DESCRIPTION OF THE DRAWINGS

The invention will be more fully understood from the following detailed description taken in conjunction with the accompanying drawings, in which:

FIG. 11 is a sectional view of the tool shown in FIG. 9, at line 11-11;

FIG. 12 is perspective view of a pusher block useful with the tool of the present invention;

FIG. 13 is a perspective view of a further embodiment of an installation tool according to the present invention;

FIG. 17 is an exploded perspective view of a slaphammer instrument for use with a medical installation tool of the present invention;

FIG. 18 is a side view illustration of a portion of a pusher rod for use with a medical installation tool according to the present invention;

DETAILED DESCRIPTION OF THE DRAWINGS

Figure 1:
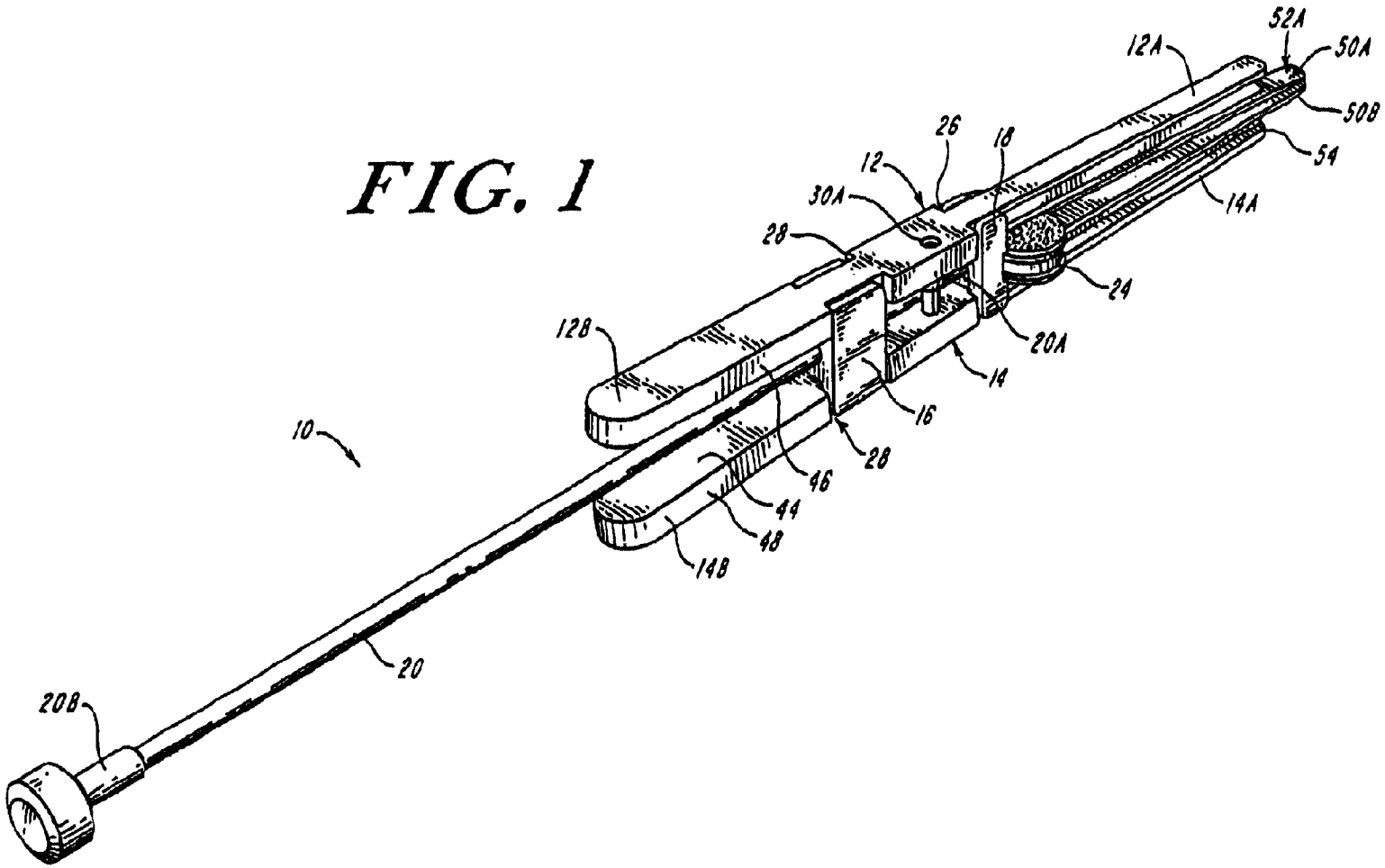
FIG. 1 is a perspective view of an installation tool according to the present invention.
Figure 2:
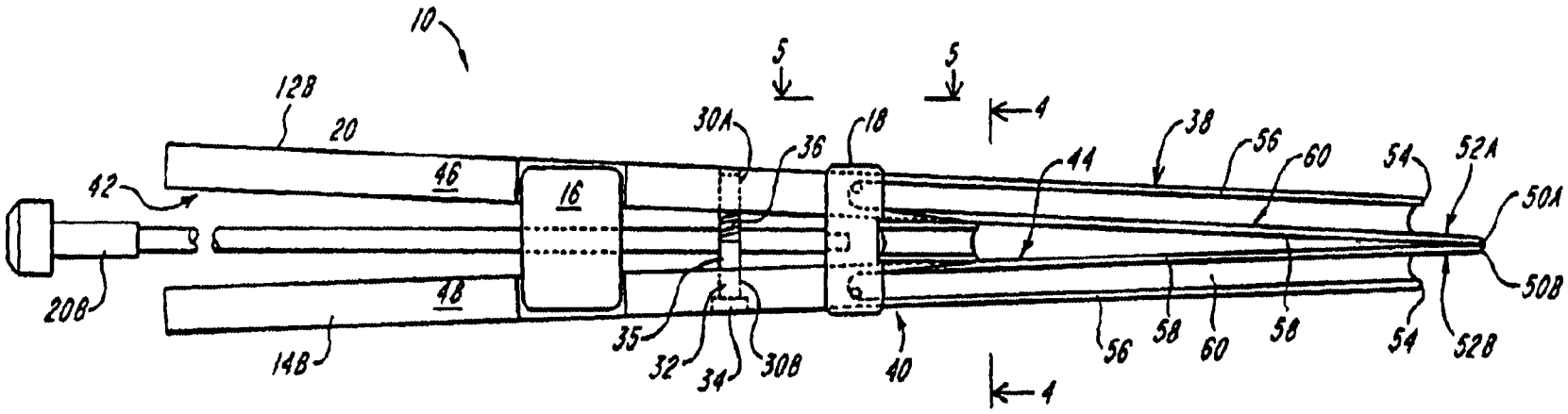
FIG. 2 is a side, elevation view of the tool shown in FIG. 1.

The present invention provides an installation tool that is useful for the efficient and effective placement of an article, such as an artificial disc or cage, between adjacent vertebral bodies. The installation tool can be provided as a kit having modular components which allow the surgeon to select from among a variety of components to assemble an installation tool that is optimized for its intended use. Although the invention is described primarily with reference to being used to install an artificial disc between adjacent vertebral bodies, it is understood that the installation tool of the invention can be used to place other elements between vertebral bodies, or in other locations within a patient's body. Exemplary elements that can be placed between vertebral bodies include, but are not limited to interbody cages, fulsion devices, spacers, grafts, and the like.

As shown in FIGS. 1-3B, the installation tool 10 of the invention includes opposed levers 12, 14, each having a distal portion 12A, 14A and a proximal, handle portion 12B, 14B. Disposed between the levers 12, 14 is a fulcrum 16 and pusher block 18, which is disposed distally of the fulcrum 16. The pusher block 18 includes a bore extending at least partially therethrough and it is selectively movable from an initial position distal of the fulcrum 16 to a final location adjacent a distal end of the levers. A pusher rod 20, which facilitates selective movement of the pusher block, has a proximal handle end 20B and a distal end 20A extending into the bore in the pusher block. Although not part of the invention, a prosthesis, such as an artificial disc 24, is positioned between the levers, distal of the pusher block 18.

Preferably the levers 12 and 14 are elongate elements that are mirror images of each other. There is no absolute top or bottom of the tool 10 since it is possible to use either surface as a "top" surface. For ease of reference, however, levers will sometimes be described herein with reference to an illustrated orientation. For example, lever 12, and components thereof, may sometimes be referred to as the top, upper, or superior lever while lever 14 may sometimes be referred to as the bottom, lower, or inferior lever.

Figure 3:
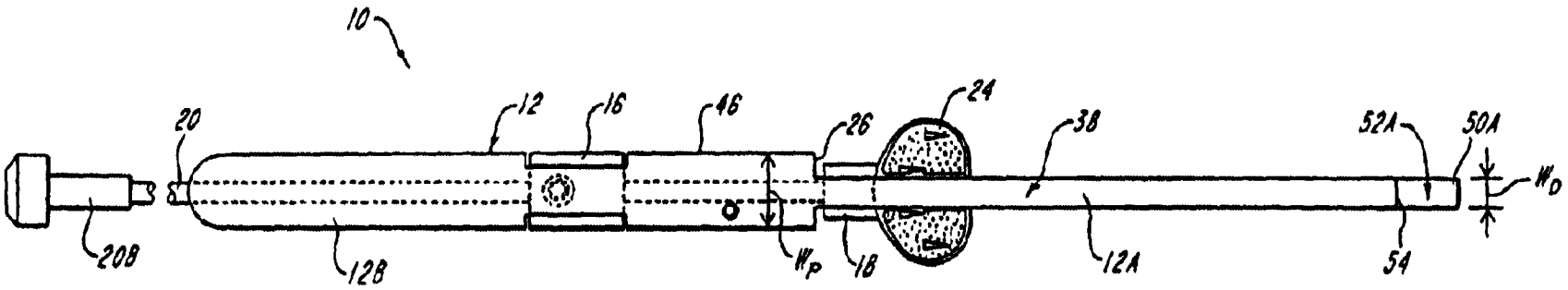
FIG. 3 is a top view of the tool shown in FIG. 1.

With further reference to FIGS. 1-3B, the levers 12, 14 include distal 12A, 14A and proximal 12B, 14B ends. The proximal end 12B, 14B of each lever may be of a shape that facilitates convenient grasping and handling of the tool. The proximal end of each lever may comprise approximately one-half of the length of each lever. In one embodiment, a shoulder 26 marks the end of the proximal portion of the tool and the beginning of the distal portion of the tool. As shown in FIGS. 1 and 3, the proximal portion of each lever preferably has a width ($W_p$) that is greater than the width ($W_d$) of the distal portion of each lever.

Figure 6:
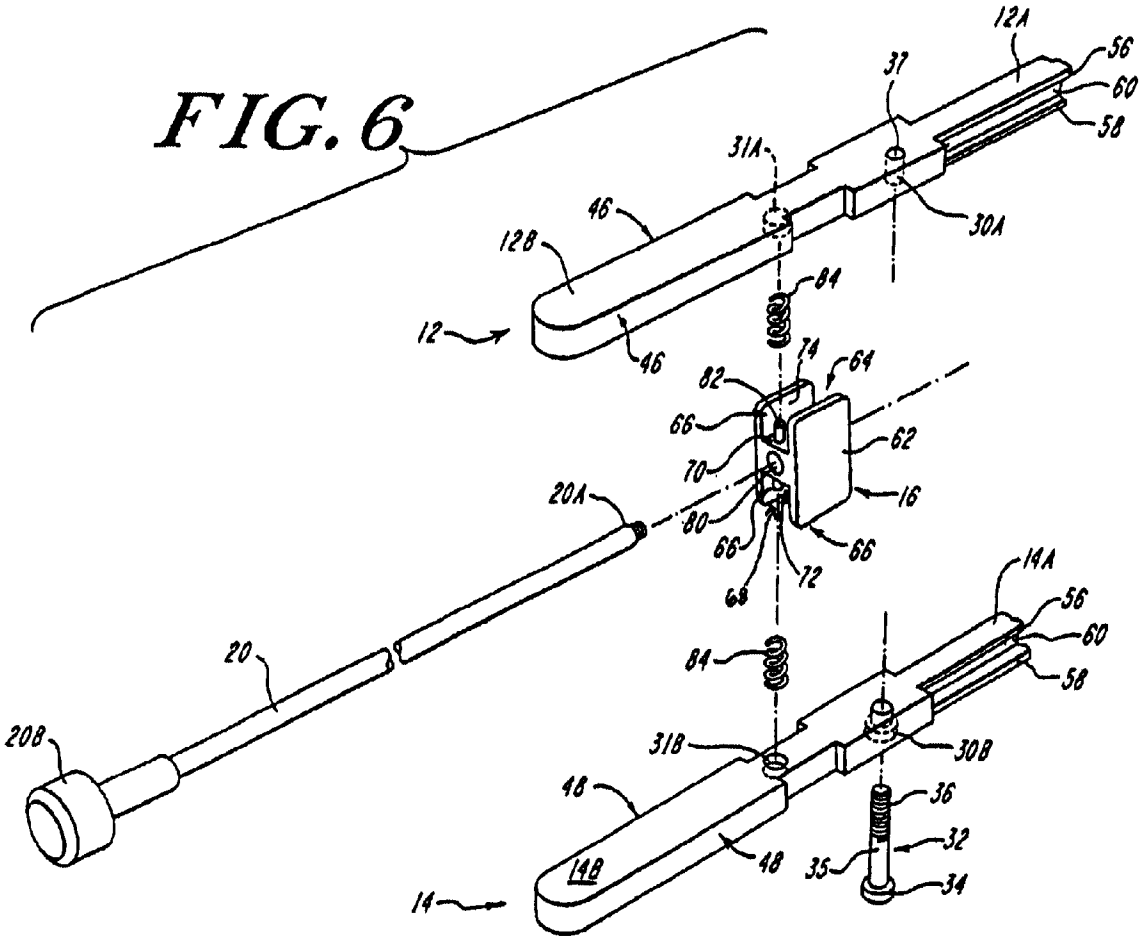
FIG. 6 is an exploded view of a proximal portion of the tool shown in FIG. 1.

The proximal portion 12B of each lever may include an indented region 28 for receiving the fulcrum 16. As shown in FIGS. 1 and 6, the indented region 28 is in the form of a substantially rectangular cut-out formed on both sides of levers 12B, 14B. This indented region 28 enables the levers to conveniently seat the fulcrum 16, as described below. The recessed region 28 is preferably formed slightly proximally of the shoulder 26. In one embodiment the distal portion of the recessed region 28 begins approximately 10 to 100 mm proximally of shoulder 26. The recessed region 28 generally has a length in the range of about 10 to 40 mm and is recessed by about 1 to 40 mm.

The proximal region of each lever 12B, 14B may also include a bore 30A, 30B which is adapted to seat a bolt 32 that enables control of the spacing between levers so that the pusher block accurately engages the metal portion of the artificial disc. As shown in FIG. 6, bolt 32 includes a head 34 and shaft 35 having a threaded region 36. Preferably, internal threads 36 are formed within bore 30A.

The distal portion of each lever 12A, 14A features side surfaces 46, 48, outwardly facing surfaces 38, 40 (illustrated as top and bottom surfaces in FIG. 6, respectively), and inwardly facing surfaces 42, 44 upon which the artificial disc 24 can ride during an installation procedure. The outwardly and inwardly facing surfaces of the lever preferably are substantially smooth. The inwardly facing surfaces 42, 44 can, however, include surface features effective to mate to complementary surface features formed on the implant. For example, each lever 12, 14 can include a rail (not shown) formed in the inwardly facing surface 42, 44 that is effective to be slidably disposed within a corresponding groove or channel formed in the implant. As a result of the surface features formed on the inwardly facing surfaces 42, 44 of the levers 12, 14, the width ($W_d$) of the distal portion of each lever can be substantially the same as or even greater than the width ($W_p$) of the proximal portion of each lever.

The distal portions 12A, 14A of the levers 12, 14 can also have blade tips 50A, 50B formed at the distal ends of the levers. The blade tips are sized and configured to facilitate their placement between vertebral bodies 201, 202. The outwardly facing surfaces 52A, 52B of blade tips may be configured to have surfaces that are beveled or radiused. In one embodiment illustrated in FIG. 3A, the blade tips $\mathbf{12}_c$C, $\mathbf{14}_c$C can be substantially curved or angled in a superior or inferior direction to facilitate placement of the blade tips $\mathbf{12}_c$C, $\mathbf{14}_c$C between adjacent vertebrae. In the illustrated embodiment, the distal tip of the rod $\mathbf{20}_c$ includes a spring 2 which allows the distal portion of the rod $\mathbf{20}_c$ to conform or bend to the shape of the curved blade tips 50A, 50B. The proximal end 4 of the spring 2 can be threadingly mated to or otherwise attached to the distal end of the rod $\mathbf{20}_c$, and the end 6 of the spring 4 can be attached to the proximal end of the pusher block $\mathbf{18}_c$. Preferably, the pusher block $\mathbf{18}_c$ includes a protrusion adapted to extend into the bore in the spring 4 to mate the pusher block $\mathbf{18}_c$ to the spring 4.

The thickness of the levers, measured at the blade tips when the tool is closed, as shown in FIG. 1, can be considerably less than the thickness of the levers measured near the fulcrum between outwardly facing surfaces 38, 40 when the tool is in the closed position. Preferably, the thickness measured at the blade tips is in the range of about 0.5 to 2 mm. A portion of each lever 12A, 14A, disposed adjacent a proximal end of the blade tips 50A, 50B, can include a stop surface 54. The stop surface 54, which is substantially vertically oriented and distally facing, is adapted to abut a vertebral body during a surgical procedure for installing an element, such as an artificial disc, between adjacent vertebral bodies. The stop surface 54 may assume a variety of configurations. In one embodiment, shown in FIGS. 2 and 8A-9, the stop surface has a substantially concave profile when viewed in the vertical plane.

Figure 4:
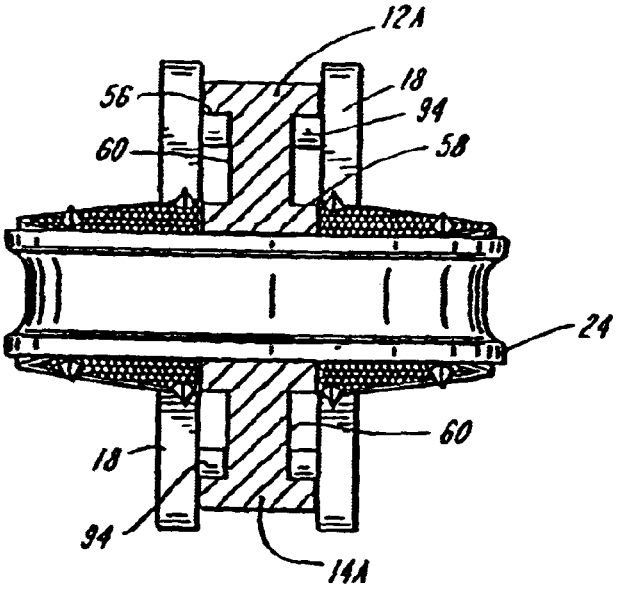
FIG. 4 is a sectional view of the tool shown in FIG. 2, at line 4-4.
Figure 5:
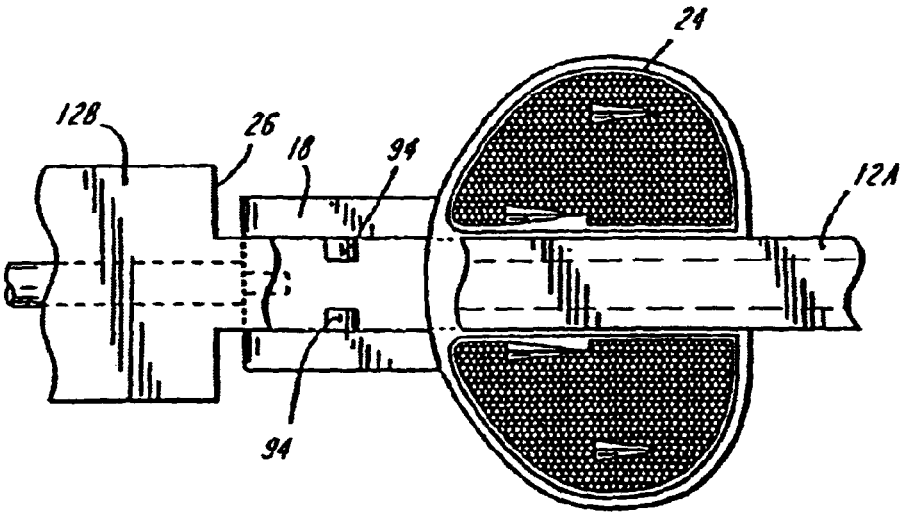
FIG. 5 is a top view of a portion of the tool shown in FIG. 2, at line 5-5.
Figure 7:
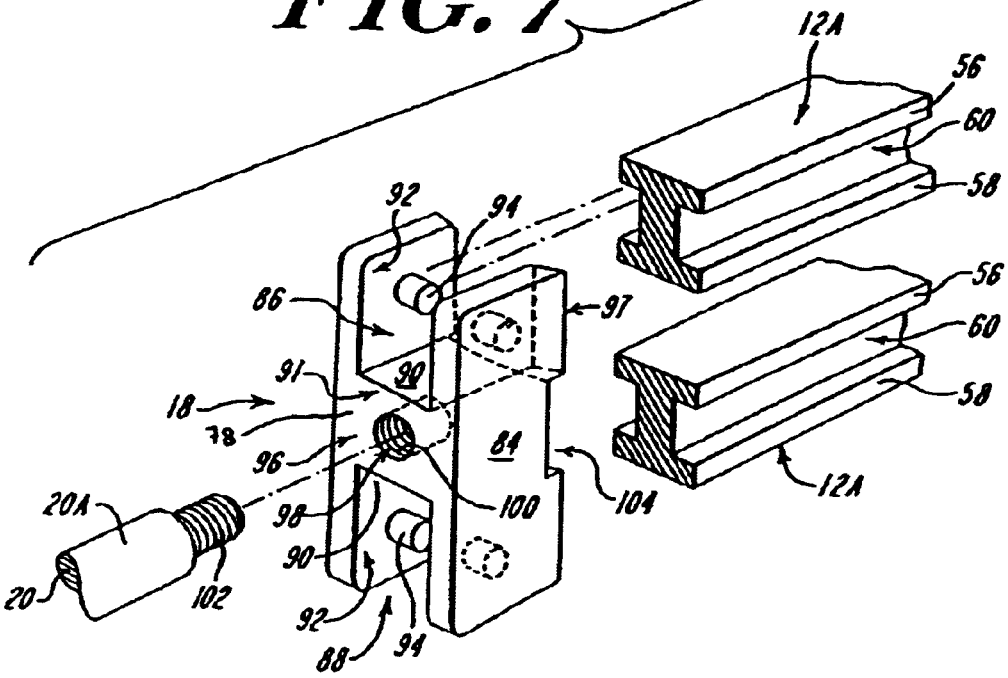
FIG. 7 is an exploded view of a portion of the tool shown in FIG. 1.

As shown in FIGS. 6-7 the side surfaces of the distal portions 12A, 14A of the levers 12, 14 may have opposed rails 56, 58, with a recessed track 60 disposed therebetween. The formation of such recessed tracks 60 within the distal side walls of levers 12, 14 causes these elements to have a profile that, as shown in FIGS. 4 and 7, is substantially I-shaped or T-shaped. The rails 56, 58 and track 60, as discussed below, can be effective to facilitate smooth and efficient movement of the pusher block.

One of ordinary skill in the art will appreciate that the size and shape of the levers may vary. Generally, however, the overall length of the levers is about 200 to 400 mm, with proximal portion 12B, 14B (proximal end to shoulder 26) having a length of about 100 to 300 mm and the distal portion 12A, 14A (shoulder 26 to blade tips) having a length of about 100 to 300 mm.

In one embodiment, illustrated in FIGS. 1-3 and 6, the fulcrum 16 is substantially a block-like object having substantially vertical side walls 62. The upper and lower surfaces 64, 66 of fulcrum 16 include recesses or grooves 68, each of which is defined by a base wall 70, 72 and opposed inner side walls 74. A core section 78 lies between the base walls 70 and 72. The core section 78 preferably includes a central bore 80 to allow passage of pusher rod therethrough. In an exemplary embodiment each base wall 70, 72 includes a mounting post 82. As shown in FIG. 6, a biasing element 84', such as a coil spring, may be placed upon each of mounting posts 82 and the mounting posts, in turn, positioned within the bores 31A, 31B of levers 12, 14.

The fulcrum 16 may assume virtually any size and shape that is able to render it effective to separate a substantially intermediate portion of levers while allowing the proximal, handle portion 12B, 14B to be closed together and result in the opening or separation of the distal portion 12A, 14A. Generally, the height of the vertical side walls 62 is in the range of about 20 to 70 mm while the height of the core section 78 (shown in FIG. 7) is in the range of about 5 to 30 mm. The length of the core section 78 may be about 5 to 40 mm.

One of ordinary skill in the art will further appreciate that the fulcrum may take on a variety of other shapes, sizes and mounting configurations. The embodiment described above is intended to represent one exemplary fulcrum design and mounting configuration.

The bolt 32, as noted above, can be used to adjust the height/spacing of the levers. One of bores 30A, 30B, has internal threads 37 that mate with threaded portion 36 of bolt 32. Tightening or loosening of the bolt will result in increasing or decreasing the spacing/distance between the levers.

The pusher block 18, as illustrated in FIG. 7, may be in the form of a substantially block-like object having vertical side walls 84 that define upper and lower recesses 86, 88 wherein each recess is defined by a base wall 90 and opposed inwardly facing side walls 92. Each inwardly facing side wall 92 preferably includes a guide post 94 that is matable within recessed tracks 60 formed in the distal portion of levers 12A, 14A.

Figure 7A:
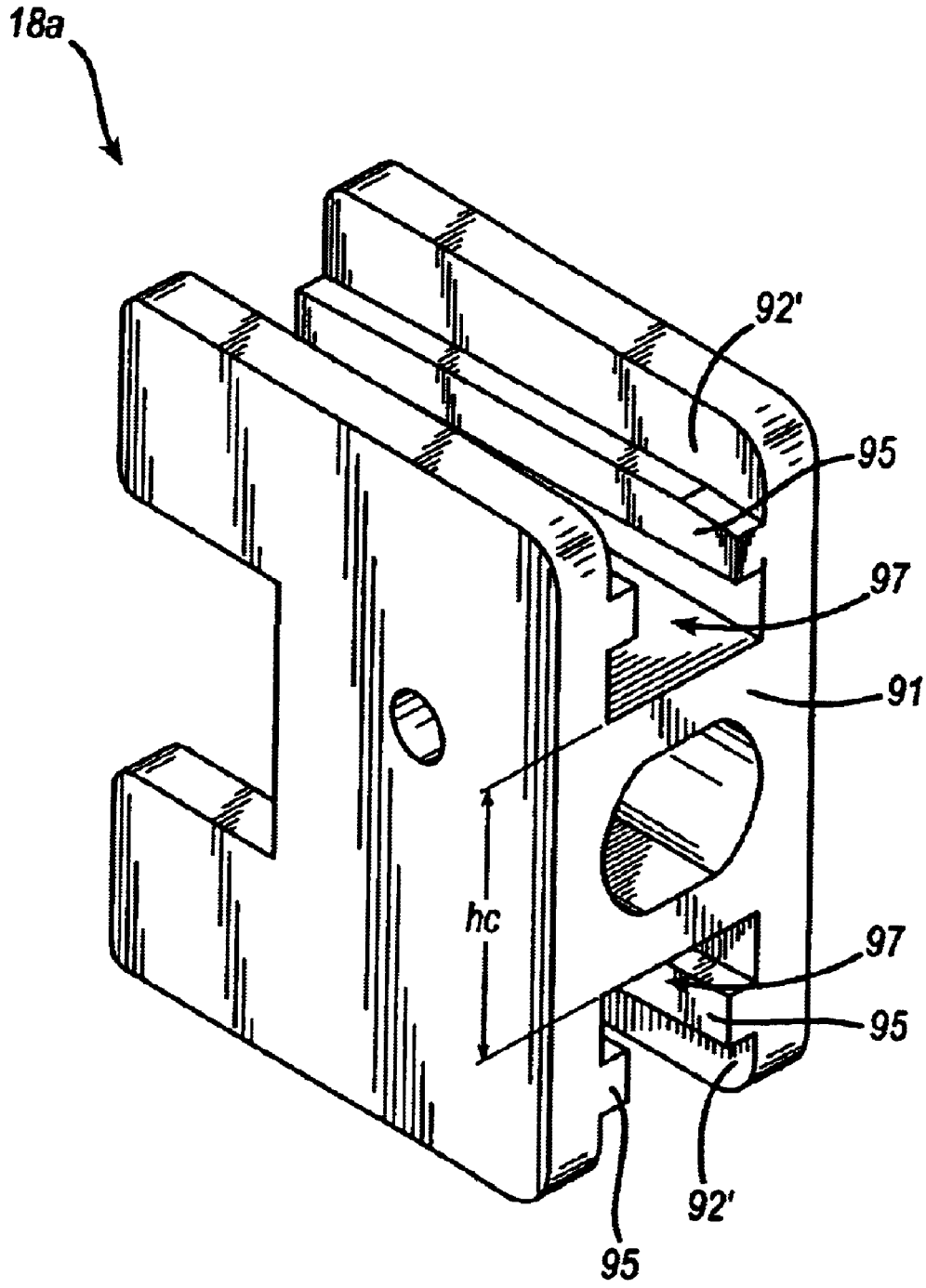
FIG. 7A is an enlarged view of another embodiment of a pusher block of the tool shown in FIGS. 1-3B.

In another embodiment, shown in FIG. 7A, each inwardly facing side wall 92' of pusher block $\mathbf{18}_a$ includes a rail 95 extending from the proximal end to the distal end of the pusher block $\mathbf{18}_a$. Each rail 95 forms a groove or track 97 that is matable with rail 56 or rail 58 of each lever 12, 14. The rail 95 and track 97 of top and bottom sides of the pusher block $\mathbf{18}_a$ limit movement of the levers 12, 14 with respect to each other. In use, proximal movement of the pusher block $\mathbf{18}_a$ is effective to cause the blade tips 50A, 50B to move to the closed position, and to cause the proximal portion of the levers 12, 14 to be fully disposed within the recesses 68 (FIG. 6) of the fulcrum 16. Once the pusher block 18 is positioned just distal to the fulcrum 16, the levers 12, 14 are in effect locked in the closed position.

Figure 8:
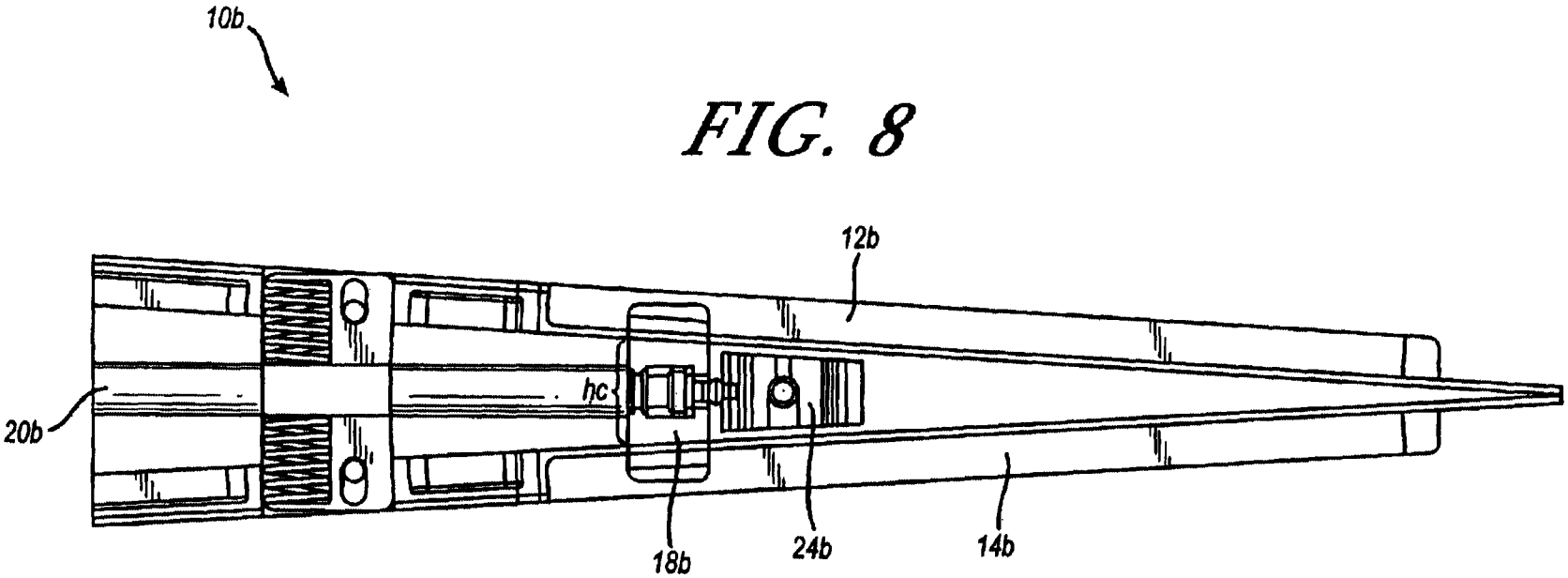
FIG. 8 is a side view of a portion of a medical installation tool according to yet another embodiment.

Referring back to FIG. 7, the core section 91 of the pusher block 18 is disposed between upper and lower base walls 90 and includes a proximally facing wall 96 and a distally facing wall 97. In one embodiment, the height of the core section 91 is less than the height of the prosthesis to be installed, thus enabling inwardly facing surfaces 42, 44 of levers 12, 14 to contact the prosthesis. Alternatively, as shown in FIG. 8, the core section 91 can have a height $h_c$ that is slightly greater than the height of the prosthesis $\mathbf{24}_b$ to prevent the prosthesis $\mathbf{24}_b$ from contacting the inwardly facing surface 42, 44 of each lever $\mathbf{12}_b$, $\mathbf{14}_b$. Thus, the prosthesis $\mathbf{24}_b$ is spaced apart from the levers $\mathbf{12}_b$, $\mathbf{14}_b$ when mated to the pusher block $\mathbf{18}_b$ or pusher rod $\mathbf{20}_b$. The distally facing wall of the pusher block 18 can have a shape which conforms to the shape of a prosthesis. In an exemplary embodiment, several pusher blocks 18, $\mathbf{18}_a$, $\mathbf{18}_b$ can be provided, each having a different size and/or shape that is optimized for use with a particular prosthesis or patient.

As noted above, a pusher rod 20 may be utilized to actuate pusher block 18. The pusher rod 20 is preferably an elongate, cylindrical member having a proximal end 20B and a distal end 20A. The rod is adapted to be positioned between the proximal ends 12B, 14B of the levers 12, 14 so that it extends into or through the bore 80 in fulcrum 16. The rod 20 can be adapted to mate to the pusher block 18 such that forward and rearward movement of the pusher rod will directly move the pusher block. Alternatively, the pusher block 18 can include a bore extending entirely therethrough, and the rod 20 can be disposed through the bore to mate directly to a prosthesis, or to mate to a connector element which, in turn, mates to a prosthesis.

Figure 3A:
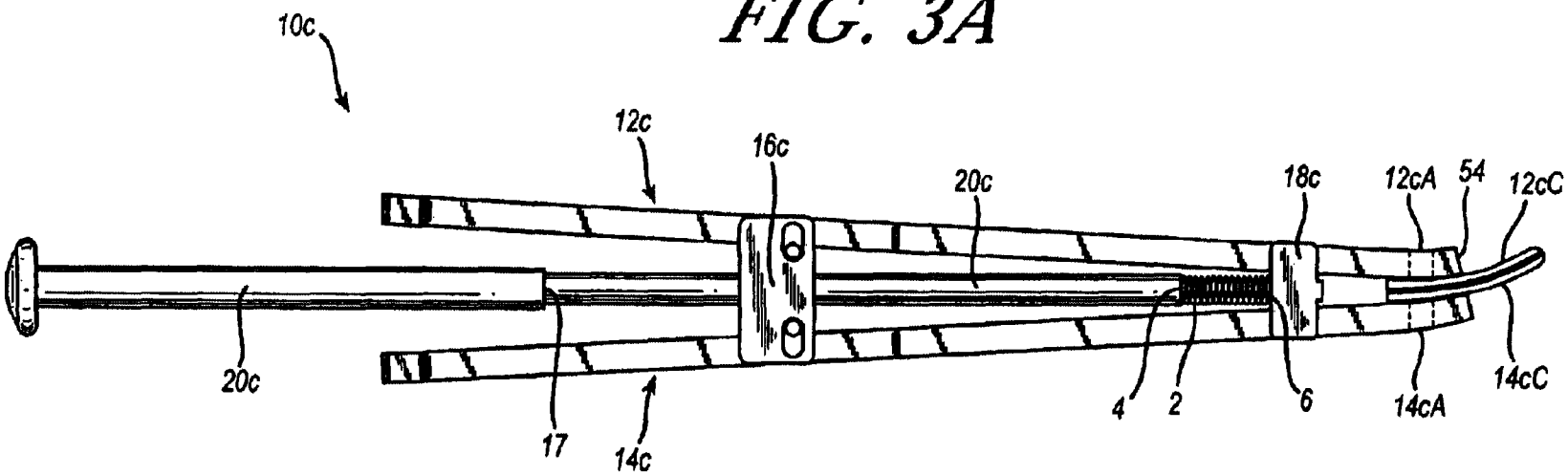
FIG. 3A is a perspective view of an installation tool having curved distal blade tips according to another embodiment of the present invention.
Figure 3B:
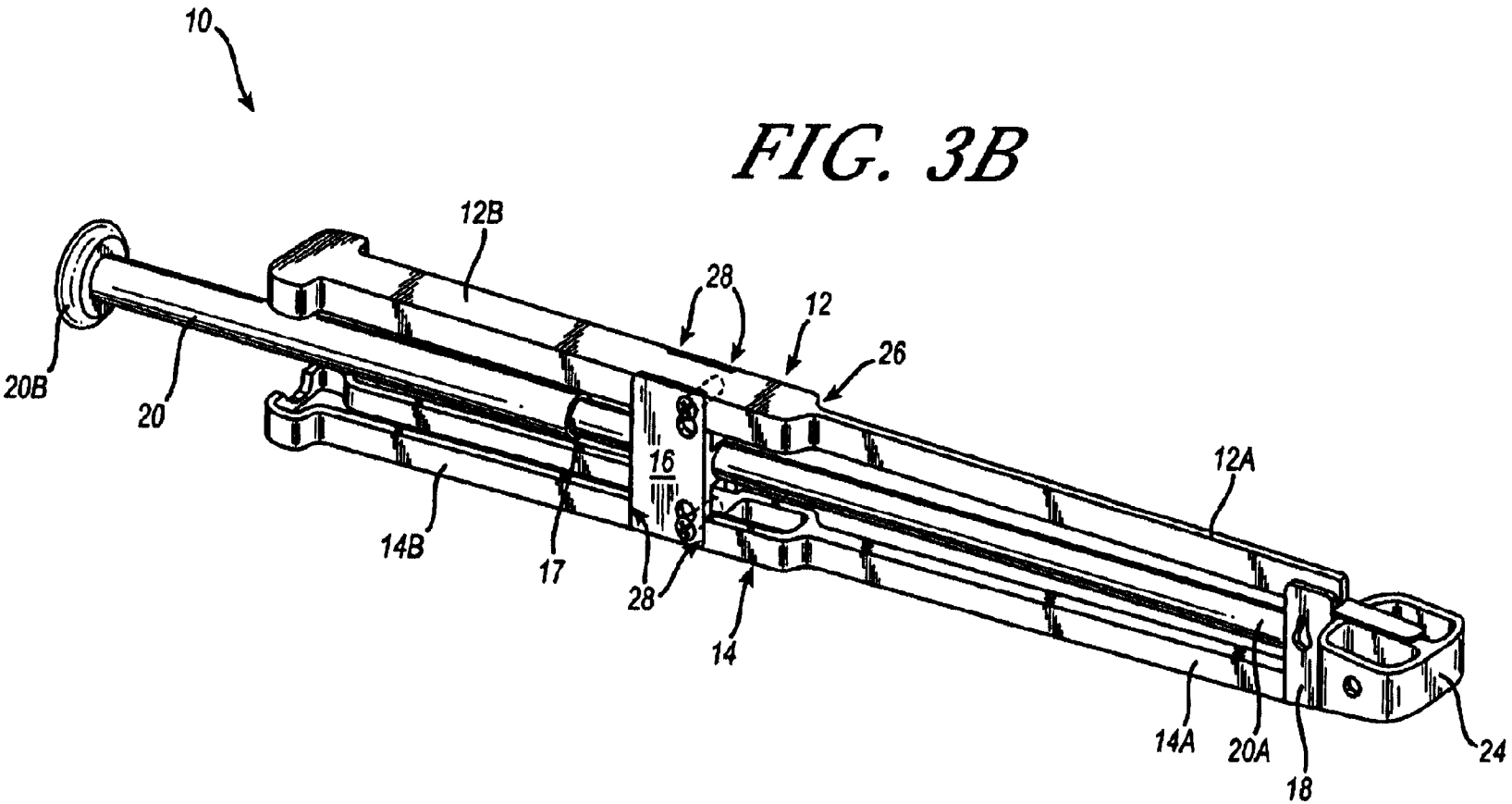
FIG. 3B is a side view illustration of another embodiment of an installation tool according to the present invention.

The pusher rod 20 can optionally include a stop feature to prevent the levers 12, 14 from being removed from the recessed formed in the pusher block. As shown in FIGS. 3A and 3B, the rod 20, $\mathbf{20}_c$ can include a stop surface 17 which abuts the proximal opening of the bore 80 in the fulcrum 16, thereby preventing proximal movement of the levers 12, 14 and fulcrum 16. The stop surface 17 can be formed by a change in diameter of the pusher rod 20, $\mathbf{20}_c$, such that the proximal portion of the rod has a diameter greater than the distal portion of the rod 20, $\mathbf{20}_c$, and greater than the bore in the pusher block 18. Alternatively, the stop surface 17 can be formed from an annular flange or similar protruding structure.

The pusher block 18 and pusher rod 20 can include a variety of features, e.g. connector elements, for joining the block 18 to the rod 20, or for mating the rod 20 and/or the block 18 to a prosthesis 24. By way of non-limiting example, FIG. 7 illustrates one embodiment in which the proximal end of the pusher block 18 facing wall includes a blind bore 98 having internal threads 100. The threads are adapted to mate with complimentary threads 102 formed on a distal end 20A of the pusher rod 20, thereby allowing the pusher rod 20 to positively engage the pusher block 18. The distal facing wall 97 of the pusher block may include a recessed region 104 that is adapted to nest artificial disc 24. As illustrated, the recessed region 104 has dimensions that enable the artificial disc to fit loosely therein. One of ordinary skill in the art will appreciate that the recessed area should have dimensions slightly greater than the dimensions of the disc so as to avoid a frictional fit that may inhibit free release of the disc from the tool. FIG. 12 illustrates one embodiment of a recessed region 104 having a contact wall 106 that has a generally arcuate shape. Preferably, contact wall 106 is substantially concave and well suited to maintaining contact over a substantial surface area of a generally curved (convex) posterior surface of an artificial disc 24.

Figure 19A:
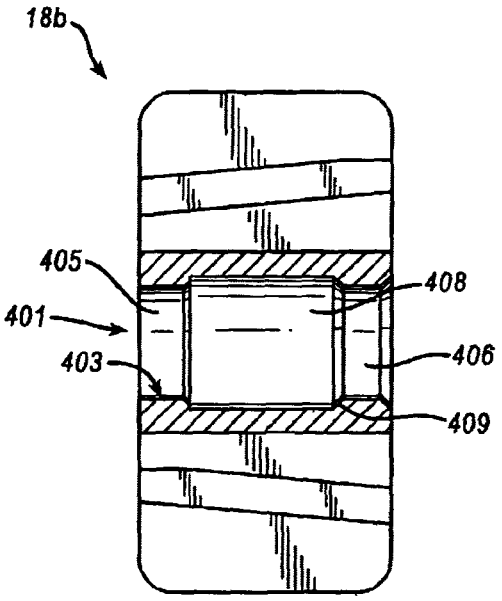
FIG. 19A is a cross-sectional side view of a pusher block component of the medical installation tool shown in FIG. 8.
Figure 19B:
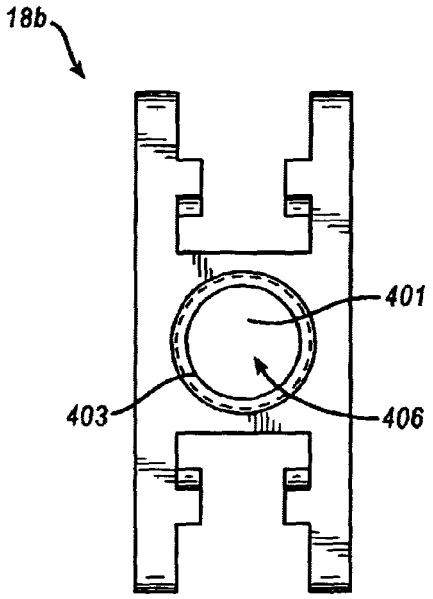
FIG. 19B is a plan view of the proximal end of the pusher block of FIG. 19A.

FIGS. 8, and 18-19B illustrate another embodiment of a connector element for joining the pusher rod $\mathbf{20}_b$ to the pusher block $\mathbf{18}_b$, and optionally to a prosthesis $\mathbf{24}_b$. As shown in FIGS. 19A and 19B, the pusher block $\mathbf{18}_b$ includes a bore 401 having a proximal opening 406, a distal opening 405, and a chamber 408 extending therebetween. The proximal and distal openings 406, 405 preferably each have substantially the same diameter, and preferably each have a diameter less than the diameter of the chamber 408. As shown in FIG. 19B, the proximal opening 406 includes a threaded region 403 which mates to a corresponding threaded region 411 formed on the rod $\mathbf{20}_b$ (FIG. 18). The proximal opening 406 can, however, include a variety of engagement elements such as, for example, an o-ring which mates to a corresponding groove formed on the rod $\mathbf{20}_b$. The distal opening 405 does not include threads, and thus is effective to prevent the threaded portion of the rod $\mathbf{20}_b$ from being threaded through the distal opening 405. The proximal opening 406 can also include a tapered portion 409 for abutting a corresponding tapered portion 410 formed on the rod $\mathbf{20}_b$.

FIG. 18 illustrates a pusher rod $\mathbf{20}_b$ that is suitable for use with the embodiment of pusher block $\mathbf{18}_b$ shown in FIGS. 19A and 19B. Pusher rod $\mathbf{20}_b$ includes a distal tip 413, a connector segment 412 extending proximally from the distal tip 413, and an annular flange 411 having a distal end 418 integral with the connector segment 412 and a proximal end 416 mated to the rod 20. The proximal and distal ends 416, 418 can be tapered to facilitate insertion and removal of the rod $\mathbf{20}_b$ from the pusher block 18. The distal tip 413 of the rod $\mathbf{20}_b$ can mate to a prosthesis, and thus can include an engagement element. As shown in FIG. 18, the distal tip 413 is threaded 415 to mate with corresponding threads formed in a bore in a prosthesis.

In use, the rod $\mathbf{20}_b$ is inserted into the proximal opening 406 of the pusher block 18. The distal tip 413 and connector segment 412 can be inserted through the bore until the threaded annular flange 411 engages the threaded region 403 of the pusher block $\mathbf{18}_b$. The flange 411 can then be rotated and thus threaded through the bore 403 to position the flange 411 in the chamber 408. Further distal movement of the rod $\mathbf{20}_b$ will insert the distal tip 413 and a substantial portion of the connector rod 412 through the distal opening 405 of the pusher block $\mathbf{18}_b$. The lack of threads, and the size differential, in the distal opening 405 will, however, prevent the annular flange 411 from exiting the chamber. Once the annular flange 411 is positioned in the chamber, the rod $\mathbf{20}_b$ is free to rotate. The rod $\mathbf{20}_b$ can then be rotated to positively engage a prosthesis, or to detach the rod from a prosthesis. In an exemplary embodiment, the threads formed on the annular flange 411 are oriented in a direction opposite to the threads 415 formed on the distal tip 413. This allows the rod $\mathbf{20}_b$ to be detached from a prosthesis without allowing the rod $\mathbf{20}_b$ to be threadingly removed through the proximal opening 406.

A person having ordinary skill in the art will appreciate that the annular flange 411, and the distal tip 413 can employ a variety of engagement elements other than threads. For example, other locking elements include snap-fit engagements, frictional engagements, bayonet-type locks, leur locks, or any other type of connector.

Figure 16:
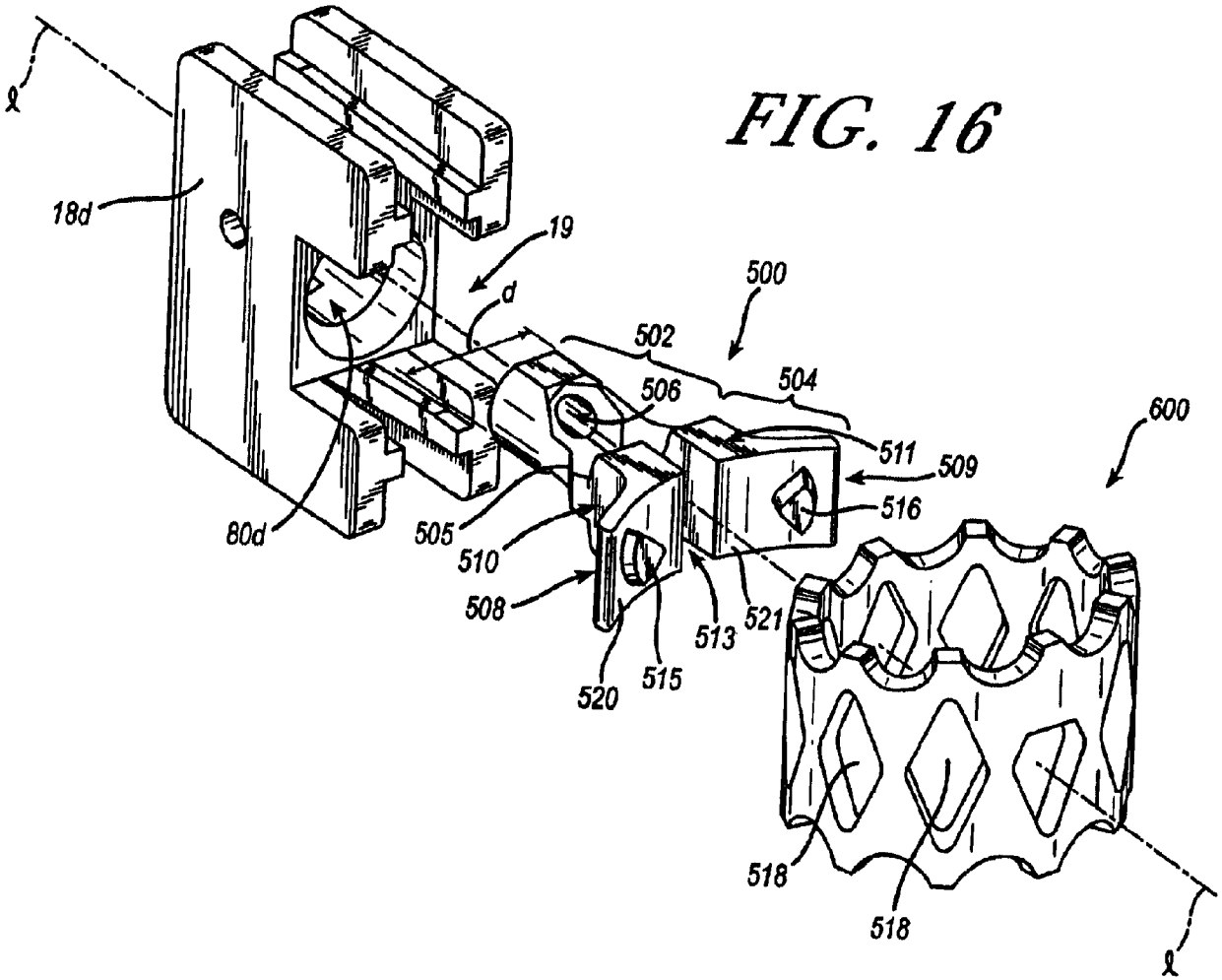
FIG. 16 is an exploded side, perspective view of one embodiment of a connector element for use with a medical installation tool.

FIG. 16 illustrates another embodiment of a connector element for joining the pusher block $\mathbf{18}_d$ to a prosthesis 600. As shown, a grasper element 500 is provided for grasping a prosthesis 600. The grasper 500 includes a proximal portion 502 and a distal portion 504. The proximal portion 502 is elongate, having a substantially cylindrical cross-section with an outer diameter d, and a bore 506 extending therethrough along the longitudinal axis l of the instrument. The bore 506 is adapted to matingly engage the distal end 20A of the rod 20, and thus can include internal threads that threadingly receive the threaded distal end 20A of the rod 20. A person having ordinary skill in the art will appreciate that a variety of alternative engagement mechanisms can be provided for mating the grasper 500 to the rod 20. The outer diameter d of the cylindrical proximal portion 502 should be less than the diameter of the bore $\mathbf{80}_d$ in the pusher block $\mathbf{18}_d$ to allow the proximal portion 502 to be inserted into the bore $\mathbf{80}_d$. The proximal portion 502 preferably includes a tapered region 505 which increases toward the distal portion 504.

The distal portion 504 of the grasper 500 is oriented to extend in a direction substantially transverse to the longitudinal axis l of the instrument and includes first and second wing-like components 508, 509, each positioned on opposed sides of the longitudinal axis l, and separated from one another by a gap 513. The first and second components 508, 509 are not attached to each other, but include a proximally extending portion 510, 511 which mates to the proximal portion 502. The proximally extending portions 510, 511 taper inwardly toward the proximal portion 502. As a result, the grasper 500 incrementally increases in diameter d toward the distal portion 504 of the grasper 500. In an exemplary embodiment, the gap 513 allows the first and second components 508, 509 to be pinched together.

The first and second components 508, 509 each include a distally facing wall 520, 521. The walls 520, 521 can have a shape that conforms to the shape of a prosthesis, and preferably the walls are slightly concave to fit around a substantially cylindrical or disc-shaped prosthesis 600, as shown. Each component 508, 509 can include a protruding element 515, 516 disposed on the distally facing wall 520, 521 that is effective to engage a prosthesis 600. The protruding elements 515, 516 can be, for example, triangle-shaped, diamond shaped, or hook-like members which, when placed into openings 518 formed in the prosthesis 600, are effective to engage the prosthesis 600.

In use, the grasper 500 is inserted into the bore $\mathbf{80}_d$ in the pusher block $\mathbf{18}_d$ and it is mated to the rod 20. The protruding elements 515, 516 are inserted into the openings 518 formed in the prosthesis 600, and the rod 20 is rotated to engage the grasper 600, thereby moving the grasper 600 proximally. As the grasper 600 is pulled in a proximal direction by the rod 20, the tapered portion of the grasper 500 is pulled into bore $\mathbf{80}_d$, thereby causing the first and second components 508, 509 to be pinched together. As a result, the protruding elements 515, 516 grasp and retain the prosthesis 600. The prosthesis 600 can then be positioned between adjacent vertebrae and, once positioned, the rod 20 can be rotated in the opposite direction to release the grasper 500, thereby allowing the first and second components 508, 509 to return to their separated state, thus releasing the prosthesis 600.

In an exemplary embodiment, the pusher block $\mathbf{18}_d$ includes a recessed region 19 formed in each of the side walls of the pusher block $\mathbf{18}_d$ to allow the grasper 500 to be inserted into the bore $\mathbf{80}_d$. The first and second components 508, 509, when mated to the pusher block $\mathbf{18}_d$, sit within the recessed region 19. The rod 20 preferably includes a stop surface (not shown) to prevent further insertion of the rod 20 through the bore $\mathbf{80}_d$ in the pusher block $\mathbf{18}_d$. The stop surface should be positioned to allow a distal portion of the rod 20 to extend through the bore $\mathbf{80}_d$ to engage the grasper 500.

The depth of insertion of the cage 600 between the vertebral bodies is dependant on the length of the grasper 500 and the depth of the recessed portion 19. For example, the length of the grasper 500 and the depth of the recessed portion 19 can be substantially the same such that the distal end of the pusher block is aligned with the distal end of the grasper. In use, the distal ends of the pusher block and the grasper align with the outer edge of the adjacent vertebrae. As a result, the implanted disc is substantially aligned with the outer edge of the adjacent vertebrae. Alternatively, the grasper 500 can have a length greater than the depth of the recessed portion 19 such that the depth of insertion of the disc is substantially equal to the different between the length of the grasper 500 and the depth of the recessed portion 19.

Figure 9:
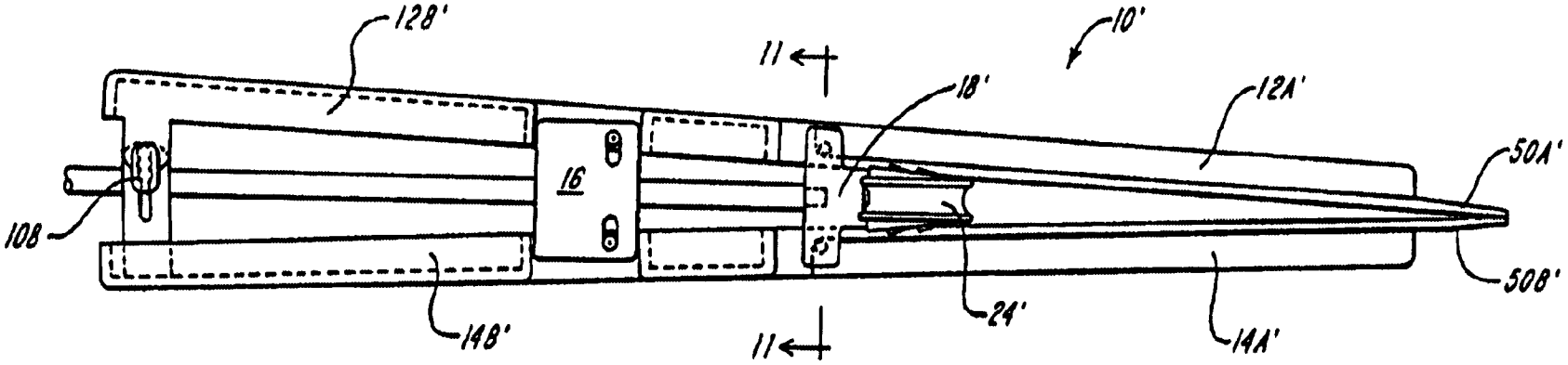
FIG. 9 is a side-elevation view of one embodiment of an installation tool according to the present invention in an initial, unlocked position.
Figure 10:
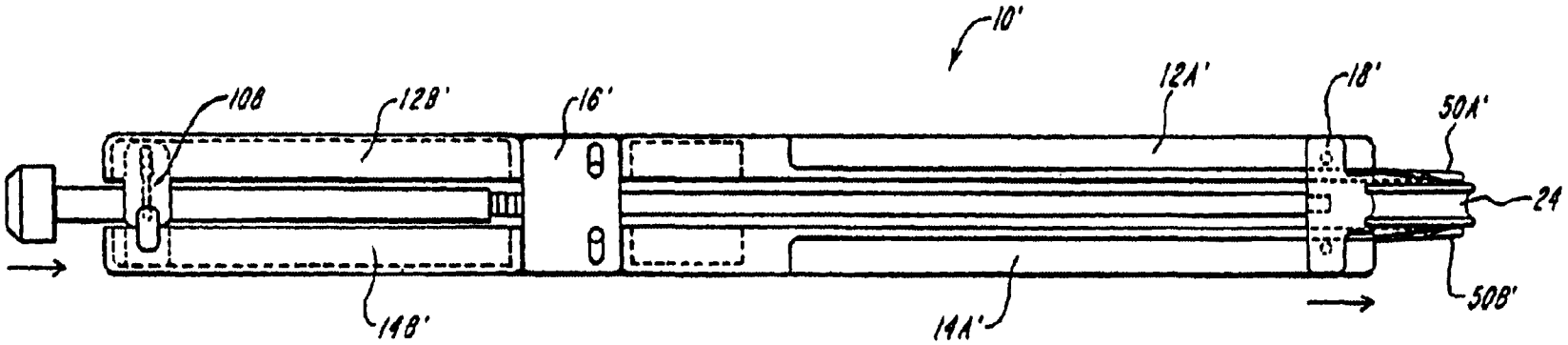
FIG. 10 is a side view of the installation tool of FIG. 9 in a final, locked position.

FIGS. 9 and 10 illustrate an alternative embodiment in which installation tool 10' includes a locking mechanism 108 in the proximal, handle portion 12B', 14B' of levers 12', 14'. The locking mechanism, which may comprise a latch and groove, simply secures the proximal handle portion of levers in a desired position and prevents complete separation of these elements. FIG. 9 illustrates the tool 10' in a position in which the proximal portion 12B', 14B' of the levers is open or unactuated. The locking mechanism 108 prevents further opening or separation of the proximal portions 12B', 14B' of the levers. However, as shown in FIG. 10, the locking mechanism still allows the handles 12B', 14B' to be actuated or closed together in order to operate the tool and install a prosthesis, such as artificial disc 24. One benefit of the locking mechanism 108 is that the disc is less likely to become inadvertently dislodged from the tool during pre-surgical installation manipulation of the tool.

FIG. 13 illustrates an embodiment of the invention in which installation tool 300 includes a plurality protrusions 302, 304 formed on proximal or handle portions 312B, 314B of levers 312, 314. Preferably, the protrusions 302, 304 are formed on lateral surfaces of the handle portions. In an exemplary embodiment two protrusions are formed on each of the top and bottom levers 312, 314. Although illustrated as being substantially cylindrical in shape, it is understood that protrusions 302, 304 may take virtually any shape. Referring back to FIG. 3B, for example, the proximal end 12B, 14B of the handles 12, 14 can have a T-shape. The T-shape, or the protrusions, may be useful to facilitate extraction of the blade tips 350A, 350B using a tool such a slaphammer 800 or a slap fork (shown in FIG. 17) The slap hammer 800 is positioned around the levers 12, 14, and slid proximally to apply a proximally directed force to the T-shaped handles, or to the protrusions 302, 304. The dimensions of T-shaped handles or the protrusions 302, 304 may vary within a wide range. Generally, however, the T-shaped handles or protrusions 302, 304 extend from the lateral surfaces of levers 312, 314 by a distance of about 3 mm to 50 mm.

Although T-shaped handles and protrusions 302, 304 are illustrated, one of ordinary skill in the art will readily appreciate that the handles can have a variety of configurations for allowing use of a slap hammer with the instrument.

With reference to FIGS. 13-15B, the installation tool 300 may also include a feature which permits selective adjustment of blade tip length (i.e., the distance between the distal end 306 of blade tips 350A, B and stop surface 354). In such an embodiment the distal portion of each of the levers 312A, 314A has a stop member component 307 and a blade member component 308, which are longitudinally separable with respect to each other. The separability of components 307 and 308 permits the blade tip length to be adjusted by varying the relative positions of components 307, 308.

Figure 14:
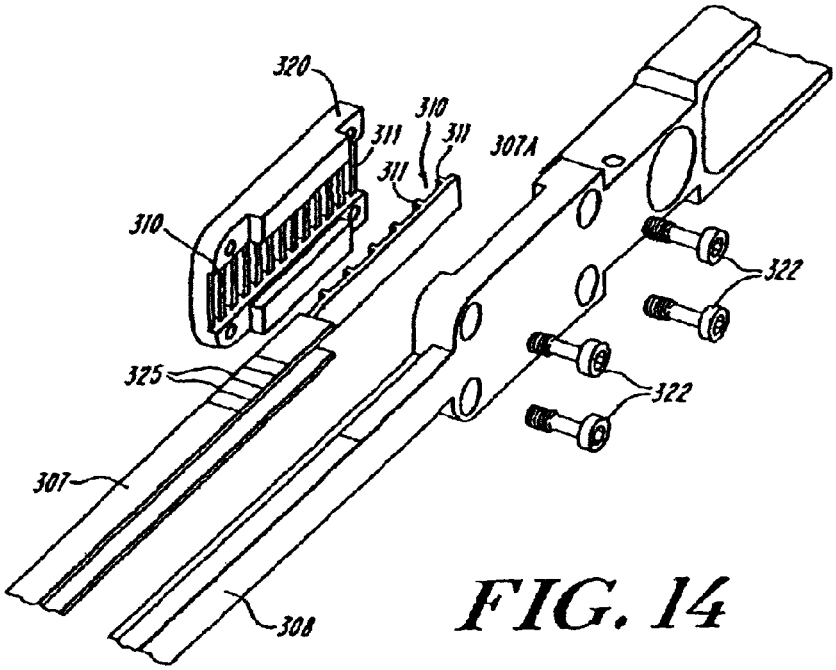
FIG. 14 is an exploded, perspective view of a portion of the installation tool shown in FIG. 13.

As shown in FIGS. 13 and 14 tool 300 includes a junction box 309 which houses and secures the components 307, 308. A portion 307A of the stop member component 307, which mates with the inner surface of the cover 320 of the junction box 309, includes a series of grooves 310 separated by raised ridges 311. Similarly, the abutting, inner surface of the cover 320 of the junction box 309 includes grooves and ridges 310, 311 as well. As further illustrated, the cover 320 is secured to levers 312, 314 by suitable fasteners, such as screws 322. Biasing elements, such as compression springs (not shown) are preferably used to bias the junction box to a position such that the grooves and ridges 310, 311 of the cover 320 and the stop member component 307 mate with and remain firmly secured to one another. As shown in FIG. 14, suitable indicia 325 may be present on the stop member component 307 to indicate the position of the stop member component 307 with respect to the blade member component. Although FIG. 14 only illustrates, in detail, the configuration of lever 12, it is understood that the same construction is used for lever 14.

Figure 15A:
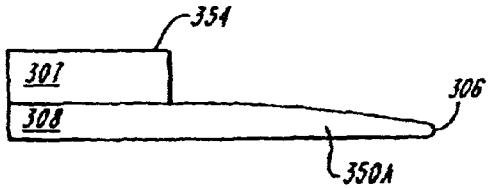
FIG. 15A is a side, elevation view of a portion of the distal end of the installation tool of FIG. 13 in a first position.
Figure 15B:
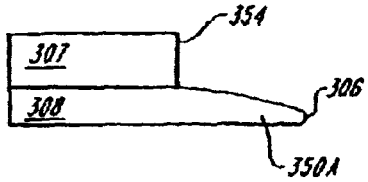
FIG. 15B is a side, elevation view of a portion of the distal end of the installation tool of FIG. 13 in a second position.

The result of this selective adjustability is shown in FIGS. 15A and 15B, in which the blade tip length is greater in FIG. 15A than in FIG. 15B.

Figure 8A:
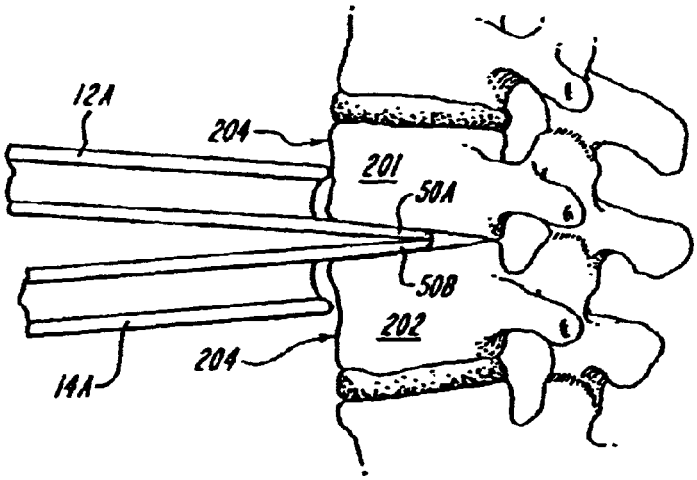
FIGS. 8A-8D illustrate, sequentially, the operation of the installation tool according to the present invention during the installation of an artificial disc.
Figure 8B:
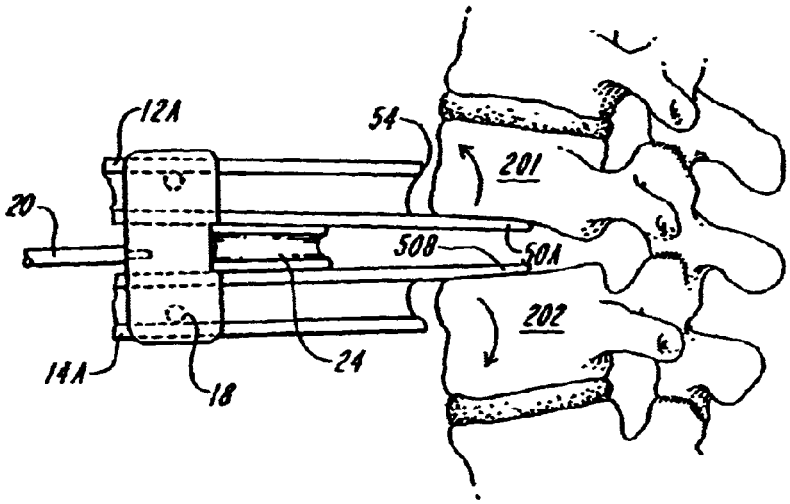
Figure 8C:
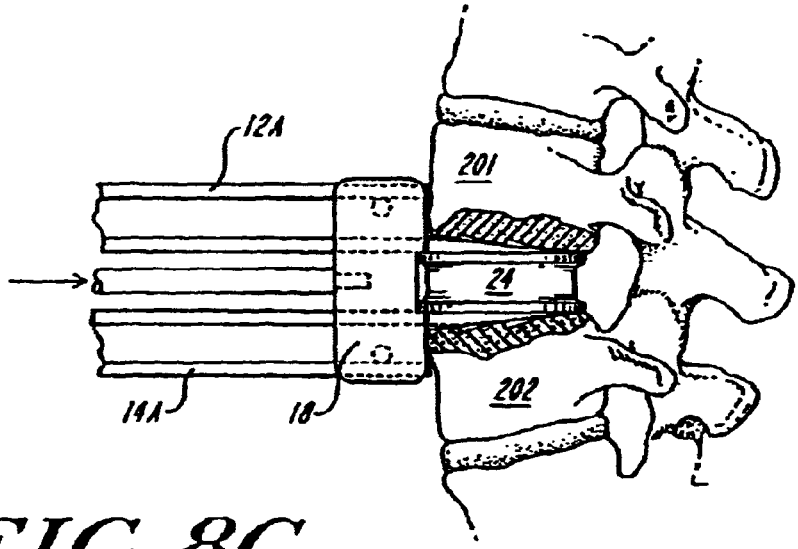
Figure 8D:
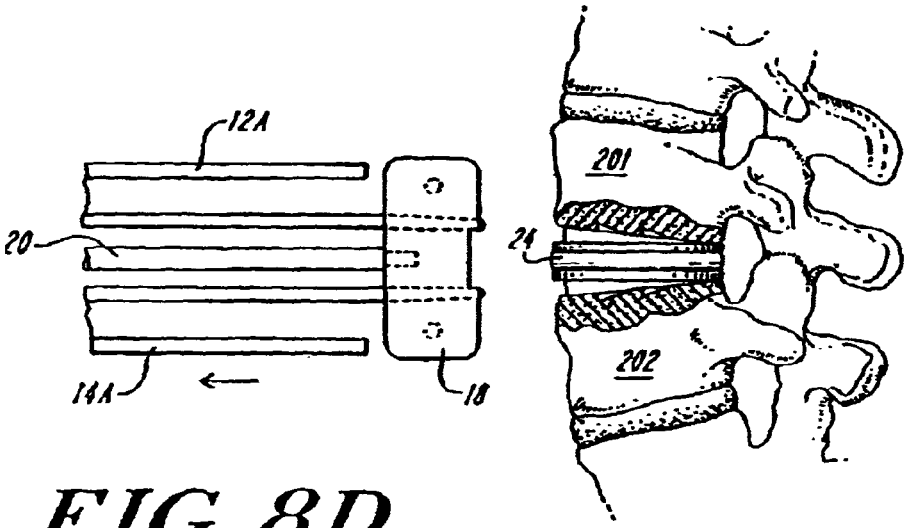

FIGS. 1 and 8A-8D sequentially illustrate the use of tool 10 for the installation of an artificial disc 24. The tool is first assembled as shown in FIG. 1, and with pusher block 18 positioned in its initial position such that its proximally facing wall 96 abuts shoulder 26, the posterior surface 27 of the disc is placed against the distal facing wall 97 of the pusher block. With the handles 12B, 14B in the open position and the blade tips 50A, B closed, the blade tips are wedged between adjacent vertebral bodies 201, 202 to effect slight separation between at least the anterior portions of the vertebral bodies. The blade tips 50A, B should be fully inserted between the vertebral bodies, as shown in FIG. 8A, so as to enable the vertebral stop surface 54 to abut the posterior side 204 of the vertebral bodies 201, 202. The pusher rod 20 is then pushed forward, causing distal movement of the pusher block 18 and artificial disc 24. The forward or distal movement of pusher block 18 and the artificial disc 24 also causes further separation of the blade tips 50A, B and thus further separation of the vertebral bodies 201, 202 as shown in FIG. 8B. Advancement of the pusher block 18 and the artificial disc 24 continues until, as shown in FIG. 8C, the disc is properly installed between adjacent vertebral bodies. FIGS. 8B and 8C illustrate that at all times separation of the vertebral bodies is only effected to the extent necessary to insert the disc. Excessive distraction or separation of the vertebral bodies does not occur because the separation of vertebral bodies is caused by the height of the pusher block.

The installation tool of the present invention can also be provided as a kit having modular components which allow the surgeon to select from among a variety of components to assemble an installation tool that is optimized for its intended use. The kit preferably includes several different rods, pusher blocks, and connectors elements, such as grasper 500, each adapted to be used with a particular implant. For example, the kit can include three types of pusher blocks, each adapted to mate with a particular prosthesis. As shown in FIG. 16, the pusher block $\mathbf{18}_d$ can be used in combination with grasper 500 to insert a cage-type spacing prosthesis. Alternatively, as shown in FIG. 1, pusher block 18 can be provided for inserting an artificial disc. A person having ordinary skill in the art will appreciate that the installation tool can include a variety of components having a combination of different features. Moreover, the components can be adapted for use with particular types of prosthesis, or for use with other components.

One of ordinary skill in the art will appreciate further features and advantages of the invention based on the above-described embodiments. Accordingly, the invention is not to be limited by what has been particularly shown and described, except as indicated by the appended claims. All publication and references cited herein are expressly incorporated herein by reference in their entity.

What is claimed is:

[1. A medical device installation kit, comprising:

a pair of opposed levers, each lever having a proximal handle portion and a distal portion;

a fulcrum disposed between the opposed levers for allowing pivotal movement of the levers with respect to each other; and a plurality of prosthesis installation assemblies adapted to be slidably disposed between the levers and slidably coupled to the fulcrum such that each prosthesis installation assembly is movable between a first, proximal position and a second, distal position, each assembly including a handle portion effective to move the prosthesis installation assembly between the first and second positions, and a distal prosthesis effecting element adapted to place a prosthesis between adjacent bone structures.]

[2. The medical device installation kit of claim 1, wherein one of the prosthesis installation assemblies comprises:

a pusher block having a proximal end, a distal end, and a bore extending therethrough;

a pusher rod slidably disposed between the levers and extending through the bore in the pusher block; and a grasping element effective to releasably engage a prosthesis.]

[3. The medical device installation kit of claim 2, wherein the grasping element has an elongate proximal portion adapted to fit within the bore of the distal end of the pusher block, and a distal portion having opposed first and second components which are movable between a first, open position, and a second, closed position that is effective to engage a prosthesis.]

[4. The medical device installation kit of claim 3, wherein a distal end of the rod threadingly engages the bore of the pusher block and wherein rotation of the rod in a first direction is effective to cause the elongate proximal portion of the grasping element to move proximally within the bore of the pusher block and move the first and second components to the second, closed position while rotation of the rod in a second direction is effective to cause the elongate proximal portion of the grasping element to move distally out of the bore of the pusher block and move the first and second components to the first, open position.]

[5. The medical device installation kit of claim 1, wherein one of the prosthesis installation assemblies comprises a pusher rod having a proximal handle portion, and distal portion having a distal tip adapted to positively engage a prosthesis.]

[6. The medical device installation kit of claim 5, wherein the prosthesis installation assembly further includes a pusher block having a proximal end, a distal end, and a bore extending therethrough, the distal portion of the pusher rod extending through the bore in the pusher block.]

[7. The medical device installation kit of claim 1, wherein one of the prosthesis installation assemblies comprises:

a pusher rod having an externally threaded first distal portion and an externally threaded second distal portion, the second distal portion having a diameter greater than a diameter of the first distal portion and being positioned proximal to the first distal portion;

a pusher block having a bore extending entirely therethrough having a threaded proximal opening that is threadingly matable with the second distal portion of the rod, and a distal opening having a diameter less than the diameter of the second distal portion of the rod; and a chamber disposed between the proximal and distal openings and having a diameter greater than the diameter of the second distal portion of the rod.]

[8. The medical device installation kit of claim 7, wherein the rod is freely rotatable when the second distal portion is disposed within the chamber of the pusher block.]

[9. The medical device installation kit of claim 8, wherein the first distal portion of the rod is adapted to positively engage a prosthesis.]

[10. The medical device installation kit of claim 1, wherein one of the prosthesis installation assemblies comprises:

a pusher block having a proximal end, a distal end, and a bore extending therethrough, the pusher block being slidably disposed between the levers;

a pusher rod having a proximal, handle portion and a distal portion extending through the bore in the pusher block; and a plurality of connector elements having a proximal portion adapted to mate to a distal tip of the pusher rod and a distal portion adapted to mate to a prosthesis.]

[11. A medical device installation tool, comprising:

a pair of opposed levers, each having a proximal, handle portion and a distal portion;

a fulcrum disposed between the two levers and including an opening extending therethrough;

a pusher block having a proximal end, a distal end, and a bore extending at least partially therethrough, the pusher block being positioned between the two levers and slidably moveable between an initial location distal of the fulcrum and a final location adjacent a distal end of the levers; and a pusher rod having a proximal, handle end, and a distal end, the pusher rod being slidably disposed through the fulcrum and the distal end of the pusher rod extending into the bore in the pusher block.]

[12. The medical device installation tool of claim 11, wherein the bore is a blind bore and the distal end of the pusher rod mates with the blind bore in the pusher block.]

[13. The medical devise installation tool of claim 11, wherein each lever includes a surface feature disposed between the proximal and distal portions thereof, the surface feature being effective to slidably mate to a complementary surface feature formed in a prosthesis.]

[14. The medical device installation tool of claim 11, wherein the bore extends entirely through the pusher block and the distal end of the pusher rod has a distal tip that is adapted to extend through the bore in the pusher block and that is effective to mate to a prosthesis.]

[15. The medical device installation tool of claim 14, wherein the pusher block has a height effective to separate the levers from a prosthesis such that, when the pusher rod is mated to a prosthesis, the levers are spaced apart from the prosthesis.]

[16. The medical device installation tool of claim 14, wherein the rod includes an externally threaded first distal portion and an externally threaded second distal portion, the second distal portion having a diameter greater than a diameter of the first distal portion and being positioned proximal to the first distal portion.]

[17. The medical device installation tool of claim 16, wherein:

the bore of the pusher block includes a threaded proximal opening that is threadingly matable with the second distal portion of the rod;

a distal opening of the pusher block having a diameter less than the diameter of the second distal portion of the rod; and a chamber disposed between the proximal and distal openings, the chamber having a diameter greater than the diameter of the second distal portion of the rod.]

[18. The medical device installation tool of claim 17, wherein the rod is freely rotatable when the second distal portion is disposed within the chamber of the pusher block.]

[19. The medical device installation tool of claim 17, wherein the threaded first distal portion of the rod is threaded in a direction opposite to the direction of the threads of the threaded second distal portion.]

[20. The medical device installation tool of claim 11, wherein the bore extends entirely through the pusher block and a distal tip of the pusher rod is adapted to extend through the bore in the pusher block, the distal tip of the pusher rod being further adapted to mate to a grasping element effective to releasably engage a prosthesis.]

[21. The medical device installation tool of claim 20, further comprising a grasping element that has an elongate proximal portion with a bore formed therein and a distal portion that is effective to releasably engage a prosthesis, the proximal portion having an outer diameter that is adapted to fit within the bore of the distal end of the pusher block.]

[22. The medical device installation tool of claim 21, wherein the distal portion of the grasping element includes opposed first and second components that are movable between a first, open position, and a second, closed position that is effective to engage a prosthesis.]

[23. The medical device installation tool of claim 22, wherein the distal end of the rod threadingly engages the bore of the grasping element, and wherein rotation of the rod in a first direction is effective to cause the elongate proximal portion of the grasping element to move proximally within the bore of the pusher block and move the first and second components to the second, closed position while rotation of the rod in a second direction is effective to cause the elongate proximal portion of the grasping element to move distally out of the bore of the pusher block and move the first and second components to the first, open position.]

[24. The medical device installation tool of claim 23, wherein the first and second components each include at least one surface feature effective to engage a prosthesis.]

[25. The medical installation tool of claim 11, wherein the bore extends entirely through the pusher block and a distal tip of the pusher rod is adapted to extend through the bore in the pusher block, the distal tip of the pusher rod being further adapted to positively engage a prosthesis.]

[26. The medical device installation tool of claim 11, wherein the pusher block has upper and lower recesses, each adapted to seat one of the levers, each of the upper and lower recesses including opposed, substantially vertical walls separated by a substantially horizontal base wall, the vertical walls each including a rail extending between the proximal and distal ends of the pusher block and effective to retain the levers.]

[27. The medical device installation tool of claim 11, wherein the handle portion of each lever is substantially T-shaped.]

[28. The medical device installation tool of claim 11, wherein the pusher rod includes a stop member effective to limit advancement of the pusher rod through the opening in the fulcrum.]

[29. The medical device installation tool of claim 11, wherein the distal portion of each lever includes a curve tip.]

*30. A medical device installation tool, comprising:*

*a pair of opposed levers movable at a distal end thereof relative to one another between a closed position and an open position;*

*a pusher block positioned between the pair of opposed levers and being movable between an initial proximal location and a final location adjacent to the distal end of the pair of opposed levers, the pusher block including projections that engage respective tracks formed in the pair of opposed levers as the projections advance distally with the pusher block; and*

*a pusher rod disposed between the pair of opposed levers and having a distal end that is coupled to the pusher block.*

*31. The medical device installation tool of claim 30, wherein each lever has an indented region formed therein that is received in one of a plurality of opposed recesses formed in a fulcrum, wherein the opposed recesses each have a generally rectangular shape.*

*32. The medical device installation tool of claim 30, wherein each lever includes opposed cut-outs formed therein and defining an indented region that is received in one of a plurality of opposed recesses formed in a fulcrum.*

*33. A medical device installation system, comprising:*

*a pair of opposed levers coupled to one another adjacent a proximal end thereof and being movable at a distal end thereof between a closed position and an open position, each lever having a surface feature formed on an inwardly facing surface thereof for engaging an implant;*

*a pusher component positioned between the pair of opposed levers and configured to distally advance an implant, the pusher component including projections which are in slidable engagement with the opposed levers during distal advancement to maintain alignment between the pusher component and the opposed levers; and*

*an implant having first and second complementary surface features formed thereon and complementary to the surface features of the opposed levers to facilitate movement of the implant with respect to the opposed levers.*

*34. The tool of claim 33, wherein the surface feature on each lever extends between the proximal and distal ends of the lever.*

*35. The tool of claim 33, wherein the surface feature on each lever comprises a rail, and the first and second surface features on the implant comprise first and second channels formed in the implant.*

*36. The tool of claim 35, wherein the pusher component comprises:*

*a pusher block movable distally towards the distal ends of the opposed levers to move the levers from the closed position to the open position; and*

*a pusher rod coupled to the pusher block such that the pusher rod is configured to advance the pusher block distally.*

*37. The tool of claim 36, wherein the projections comprise a plurality of posts extending from the pusher block, each post being complementary to a track formed in each lever such that the post is configured to slide along the track to facilitate movement of the pusher block with respect to the opposed levers.*

*38. The tool of claim 33, wherein at least one of the opposed levers includes a stop feature located on a distal portion thereof and configured to engage a vertebral body to stop further distal movement of the opposed levers.*

*39. The tool of claim 38, wherein the stop feature comprises a vertically oriented, distally facing surface located on the distal portion of at least one of the opposed levers.*

*40. A medical device installation system, comprising:*

*a first lever having proximal and distal ends, the first lever having a first rail formed thereon;*

*a second lever having proximal and distal ends, the second lever being coupled to the first lever at a location proximal to the distal ends of the first and second levers, the second lever having a second rail formed thereon;*

*an implant having first and second grooves formed in opposed surfaces thereof for seating the first and second rails to facilitate slidable movement of the implant with respect to the first and second levers; and*

*a pusher block disposed between the first and second levers and slidably movable towards the distal ends of the first and second levers to distally advance the implant.*

*41. The system of claim 40, further comprising a pusher rod coupled to the pusher block and configured to advance the pusher block distally towards the distal ends of the first and second levers.*

*42. The system of claim 41, wherein the pusher block includes a bore formed therein for receiving a distal end of the pusher rod.*

*43. The system of claim 40, wherein the pusher block includes a plurality of posts extending therefrom, with a first post of the plurality of posts being configured to slide along a first track formed in the first lever and a second post of the plurality of posts being configured to slide along a second track formed in the second lever to facilitate movement of the pusher block with respect to the first and second levers.*

*44. The system of claim 40, wherein at least one of the first and second levers includes a stop feature located on a distal portion thereof and configured to engage a vertebral body to stop further distal movement of the respective lever.*

*45. The system of claim 44, wherein the stop feature further comprises a vertically oriented, distally facing surface located on the distal portion of at least one of the first and second levers.*

* * * * *